United States Patent
Smith et al.

(10) Patent No.: US 11,229,464 B2
(45) Date of Patent: Jan. 25, 2022

(54) APPARATUS FOR DRIVER-SPECIFIC BACKOUT PREVENTION

(71) Applicant: Medos International Sarl, Le Locle (CH)

(72) Inventors: Keanan R. Smith, Quincy, MA (US); Joshua Rodriguez, East Providence, RI (US); Raymond F. Murphy, Attleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 118 days.

(21) Appl. No.: 16/703,093

(22) Filed: Dec. 4, 2019

(65) Prior Publication Data

US 2021/0169538 A1    Jun. 10, 2021

(51) Int. Cl.
*A61B 17/86* (2006.01)
*A61B 17/02* (2006.01)
*A61B 17/80* (2006.01)
*A61B 17/00* (2006.01)

(52) U.S. Cl.
CPC ........ *A61B 17/8615* (2013.01); *A61B 17/025* (2013.01); *A61B 17/0218* (2013.01); *A61B 17/8038* (2013.01); *A61B 17/861* (2013.01); *A61B 2017/00477* (2013.01); *A61B 2017/00526* (2013.01); *A61B 2017/0256* (2013.01); *A61B 2017/8655* (2013.01)

(58) Field of Classification Search
CPC ...... A61B 17/8615; A61B 2017/00477; A61B 17/861; A61B 17/8038
See application file for complete search history.

(56) References Cited

U.S. PATENT DOCUMENTS

| 4,874,375 A | 10/1989 | Ellison |
| 5,728,046 A | 3/1998 | Mayer et al. |
| 5,876,332 A | 3/1999 | Looney |

(Continued)

FOREIGN PATENT DOCUMENTS

| WO | 2010121291 A1 | 10/2010 |
| WO | 2016/131077 A1 | 8/2016 |

OTHER PUBLICATIONS

[No Author Listed] MIT Lateral Platform, "Surgical Technique Guide," DePuy Spine Inc., 2012.

(Continued)

*Primary Examiner* — Christian A Sevilla
(74) *Attorney, Agent, or Firm* — Barnes & Thornburg LLP

(57) ABSTRACT

A driver-specific back-out prevention mechanism is disclosed that includes a screw and a body. A first driver can be used for coupling and decoupling the screw with the body, and a second driver can only be used for adjusting the position of the screw in the receiving body. The body includes a cavity for receiving a head of the screw, with the cavity having an inward flange. The screw includes upper and lower sockets, with a channel extending though the head from the lower socket and a lock body disposed in the channel. Engagement with the first driver allows the locking body to move such that the fastener can be inserted and removed from the body. Engagement with the second driver displaces the locking body such that the locking body interferes with the flange such that screw fastener cannot be removed from the body by the second driver.

23 Claims, 19 Drawing Sheets

(56) References Cited

U.S. PATENT DOCUMENTS

| | | |
|---|---|---|
| 5,899,627 A | 5/1999 | Dobrovolny |
| 5,931,777 A | 8/1999 | Sava |
| 5,944,658 A | 8/1999 | Koros et al. |
| 6,083,154 A | 7/2000 | Liu et al. |
| 6,234,961 B1 | 5/2001 | Gray |
| 6,254,532 B1 | 7/2001 | Paolitto et al. |
| 6,322,500 B1 | 11/2001 | Sikora et al. |
| 6,350,265 B1* | 2/2002 | Blaustein ............ A61B 17/8071 606/300 |
| 6,602,190 B2 | 8/2003 | Dobrovolny |
| 6,951,538 B2 | 10/2005 | Ritland |
| 7,179,261 B2 | 2/2007 | Sicvol et al. |
| 7,491,168 B2 | 2/2009 | Raymond et al. |
| 7,611,460 B2 | 11/2009 | Dobrovolny |
| 7,846,190 B2* | 12/2010 | Ball ...................... B25B 15/005 606/313 |
| 7,918,792 B2 | 4/2011 | Drzyzga et al. |
| 7,959,564 B2 | 6/2011 | Ritland |
| 7,963,982 B2* | 6/2011 | Kirschman ........ A61B 17/8052 606/305 |
| 8,162,827 B2 | 4/2012 | Abdelgany et al. |
| 8,202,216 B2 | 6/2012 | Melkent et al. |
| 8,409,087 B2 | 4/2013 | Ames et al. |
| 8,535,320 B2 | 9/2013 | Woolley et al. |
| 8,636,655 B1 | 1/2014 | Childs |
| 8,668,715 B2 | 3/2014 | Sandhu |
| 8,715,175 B2 | 5/2014 | Assaker et al. |
| 8,894,573 B2 | 11/2014 | Loftus et al. |
| 8,974,381 B1 | 3/2015 | Lovell et al. |
| 9,050,146 B2 | 6/2015 | Woolley et al. |
| 9,078,635 B2 | 7/2015 | Menendez et al. |
| 9,216,016 B2 | 12/2015 | Fiechter et al. |
| 9,307,972 B2 | 4/2016 | Lovell et al. |
| 9,386,971 B1 | 7/2016 | Casey et al. |
| 9,414,828 B2 | 8/2016 | Abidin et al. |
| 9,545,250 B2 | 1/2017 | Pfabe et al. |
| 9,572,560 B2 | 2/2017 | Mast et al. |
| 9,649,099 B1 | 5/2017 | Casey et al. |
| 9,693,762 B2 | 7/2017 | Reimels |
| 9,700,293 B2 | 7/2017 | Cryder et al. |
| 9,801,667 B2 | 10/2017 | Hawkes et al. |
| 9,962,147 B2 | 5/2018 | O'Connell et al. |
| 10,076,320 B2 | 9/2018 | Mast et al. |
| 10,463,402 B2 | 11/2019 | Biester et al. |
| 2002/0188296 A1* | 12/2002 | Michelson ........ A61B 17/8009 606/71 |
| 2005/0131408 A1 | 6/2005 | Sicvol et al. |
| 2005/0228400 A1 | 10/2005 | Chao et al. |
| 2005/0245929 A1 | 11/2005 | Winslow et al. |
| 2006/0052671 A1 | 3/2006 | McCarthy |
| 2007/0043379 A1* | 2/2007 | Sullivan, Jr. ........ A61B 17/888 606/104 |
| 2007/0093823 A1 | 4/2007 | Booth et al. |
| 2007/0213715 A1 | 9/2007 | Bridwell et al. |
| 2008/0021285 A1 | 1/2008 | Drzyzga et al. |
| 2008/0097444 A1* | 4/2008 | Erickson ............ A61B 17/8052 606/281 |
| 2009/0093684 A1 | 4/2009 | Schorer |
| 2009/0105547 A1 | 4/2009 | Vayser et al. |
| 2009/0149885 A1 | 6/2009 | Durward et al. |
| 2009/0187080 A1 | 7/2009 | Seex |
| 2009/0216087 A1 | 8/2009 | Bjork |
| 2009/0254187 A1 | 10/2009 | Bjork |
| 2010/0317928 A1 | 12/2010 | Subramaniam |
| 2011/0004248 A1 | 1/2011 | Abdou |
| 2011/0034779 A1 | 2/2011 | Louftus et al. |
| 2011/0137345 A1 | 6/2011 | Stoll et al. |
| 2012/0089150 A1 | 4/2012 | Smith |
| 2012/0232350 A1 | 9/2012 | Seex |
| 2014/0074166 A1 | 3/2014 | Scarrow et al. |
| 2014/0194697 A1 | 7/2014 | Seex |
| 2014/0277163 A1 | 9/2014 | Kretzer et al. |
| 2014/0296917 A1 | 10/2014 | Donner et al. |
| 2015/0148853 A1 | 5/2015 | Hawkes et al. |
| 2015/0313585 A1 | 11/2015 | Abidin et al. |
| 2016/0074029 A1 | 3/2016 | O'Connell et al. |
| 2016/0106408 A1 | 4/2016 | Ponmudi et al. |
| 2016/0296220 A1 | 10/2016 | Mast et al. |
| 2016/0354073 A1 | 12/2016 | Nel et al. |
| 2016/0354074 A1* | 12/2016 | Miller .................. A61B 17/863 |
| 2017/0014117 A1 | 1/2017 | Capote |
| 2017/0014118 A1 | 1/2017 | Capote |
| 2017/0014119 A1 | 1/2017 | Capote et al. |
| 2017/0095281 A1* | 4/2017 | Kirschman ........ A61B 17/8052 |
| 2017/0105770 A1 | 4/2017 | Woolley et al. |
| 2017/0135735 A1 | 5/2017 | Hawkes et al. |
| 2018/0014858 A1 | 1/2018 | Biester et al. |
| 2018/0116758 A1 | 5/2018 | Schlosser et al. |
| 2018/0185071 A1* | 7/2018 | Altarac ............. A61B 17/7059 |
| 2018/0303473 A1 | 10/2018 | Spann et al. |
| 2019/0090864 A1 | 3/2019 | Medeiros et al. |
| 2019/0090979 A1 | 3/2019 | Medeiros et al. |

OTHER PUBLICATIONS

[No Author Listed] [No Date Given] "NuVasive MAS TLIF Surgical Technique," (25 pages).

[No Author Listed] "NuVasive MAS TLIF 2 Surgical Technique," NuVasive Inc., 2016 (48 pages).

[No Author Listed] PIPELINE Access System and CONCORDE, "Surgical Technique—Guide and Protect Catalogue," DePuy Spine Inc., 2011.

International Search Report and Written Opinion for Application No. PCT/EP2020/083321, dated Apr. 9, 2021 (13 pages).

* cited by examiner

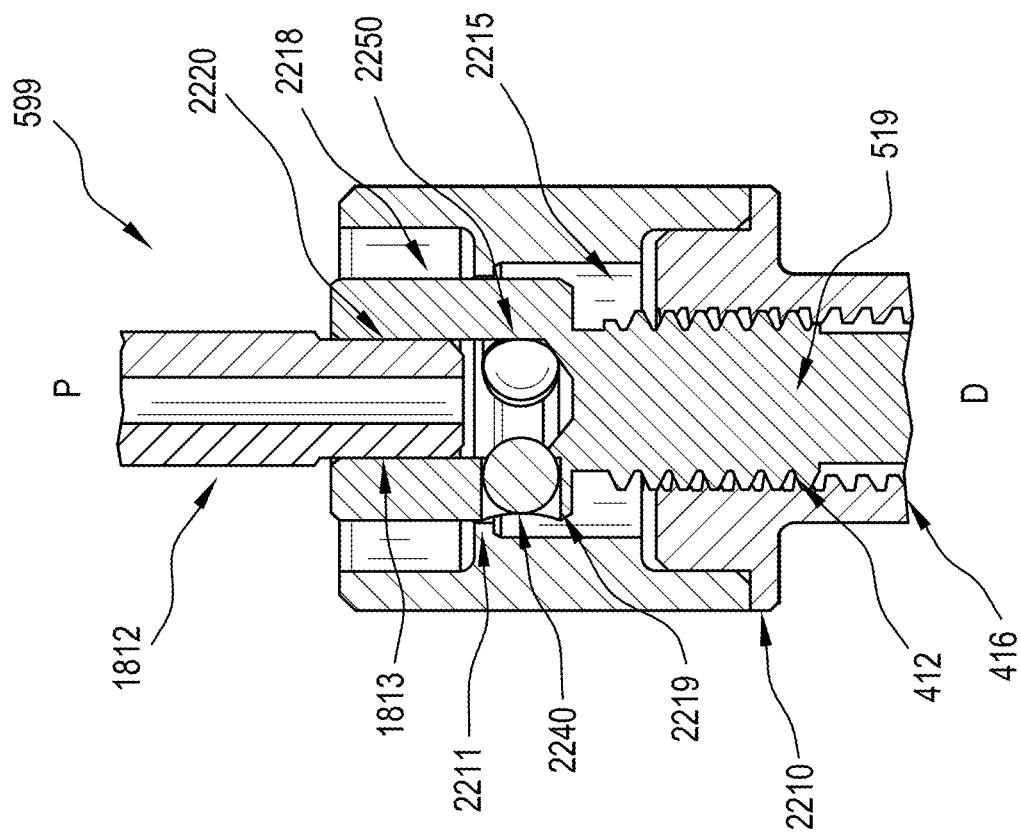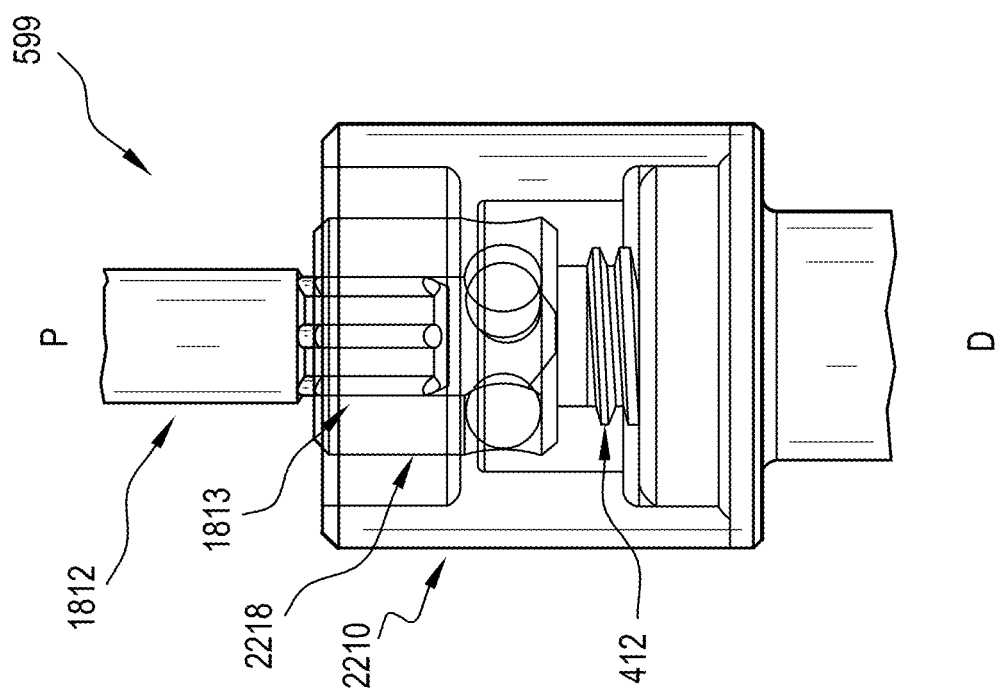

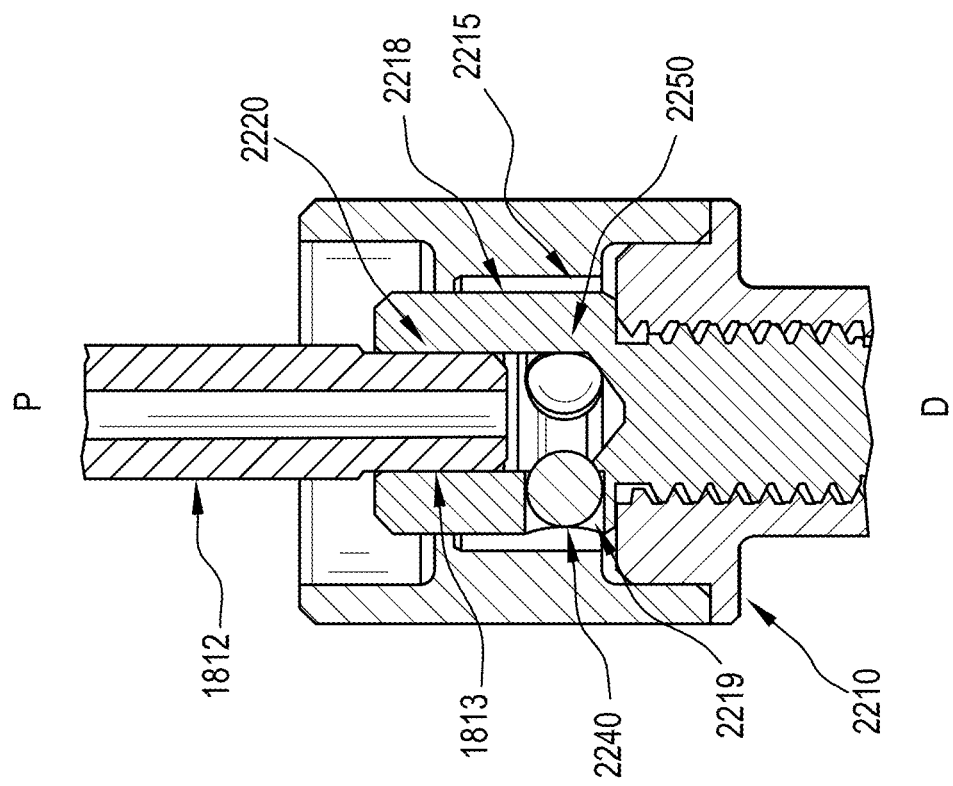
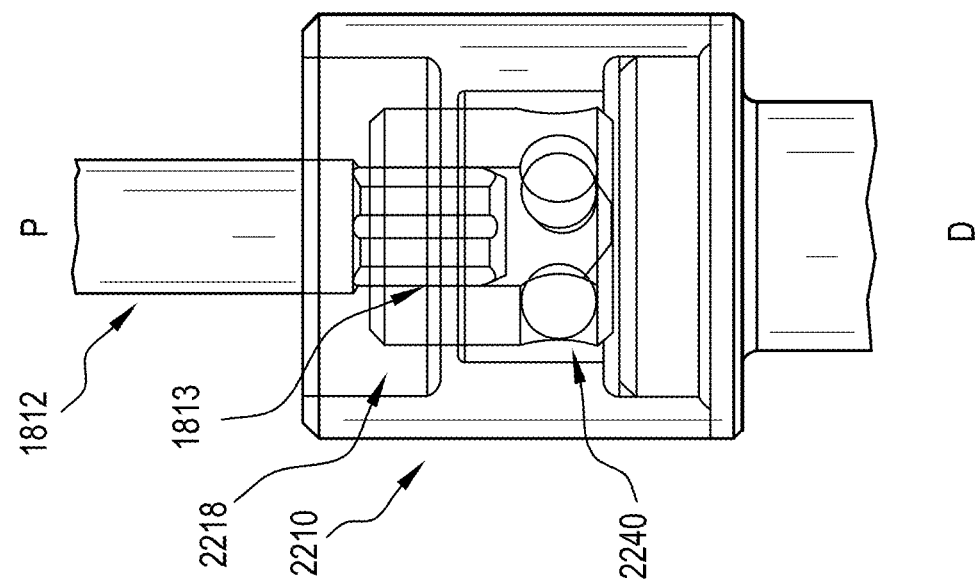

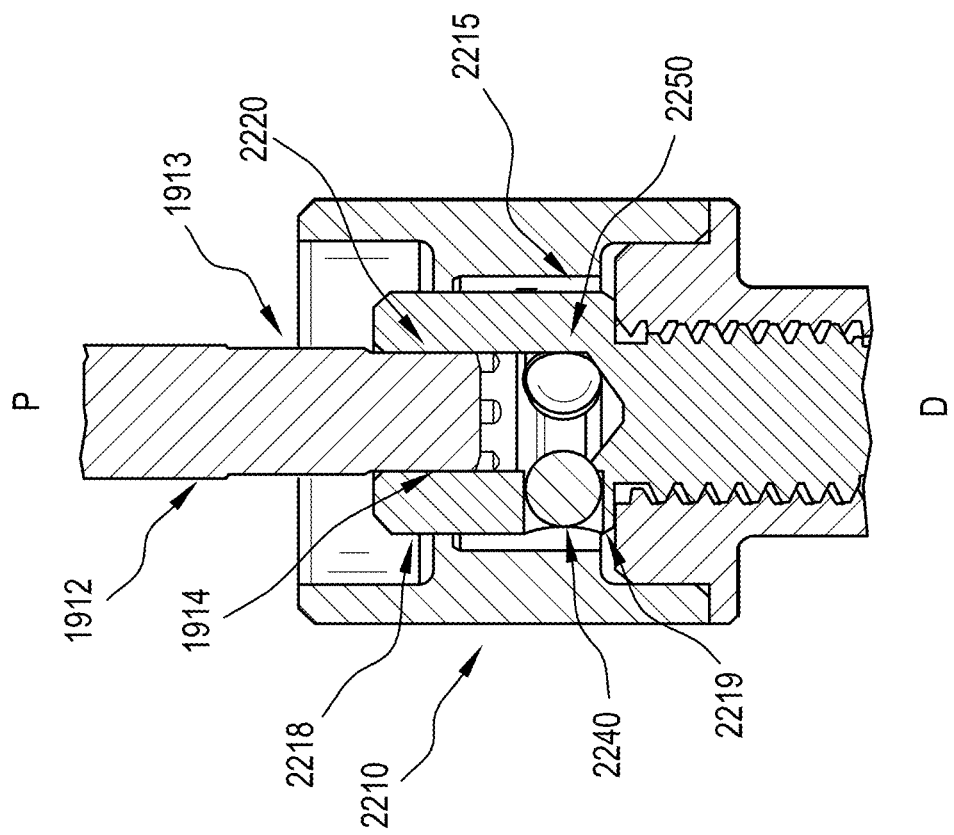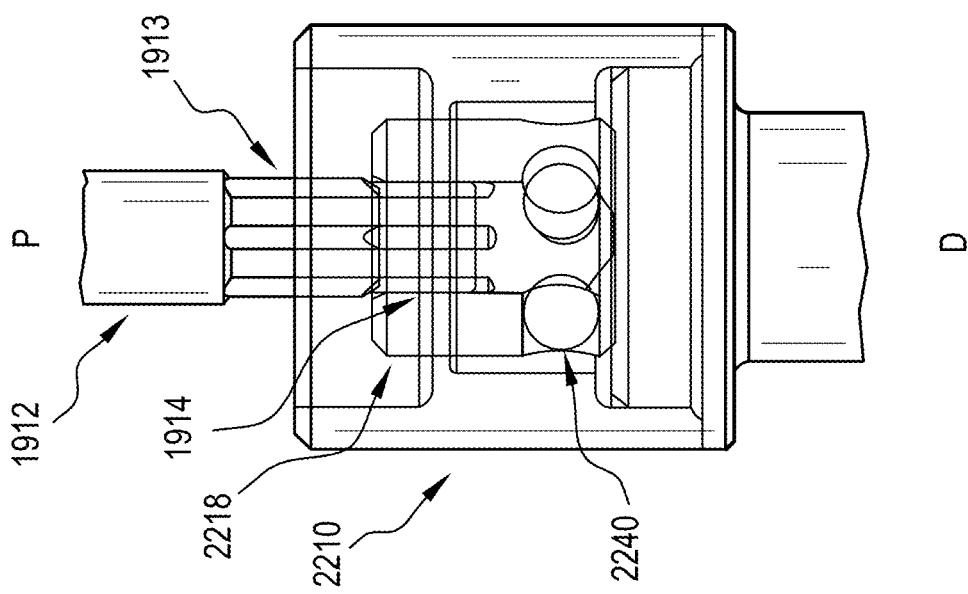

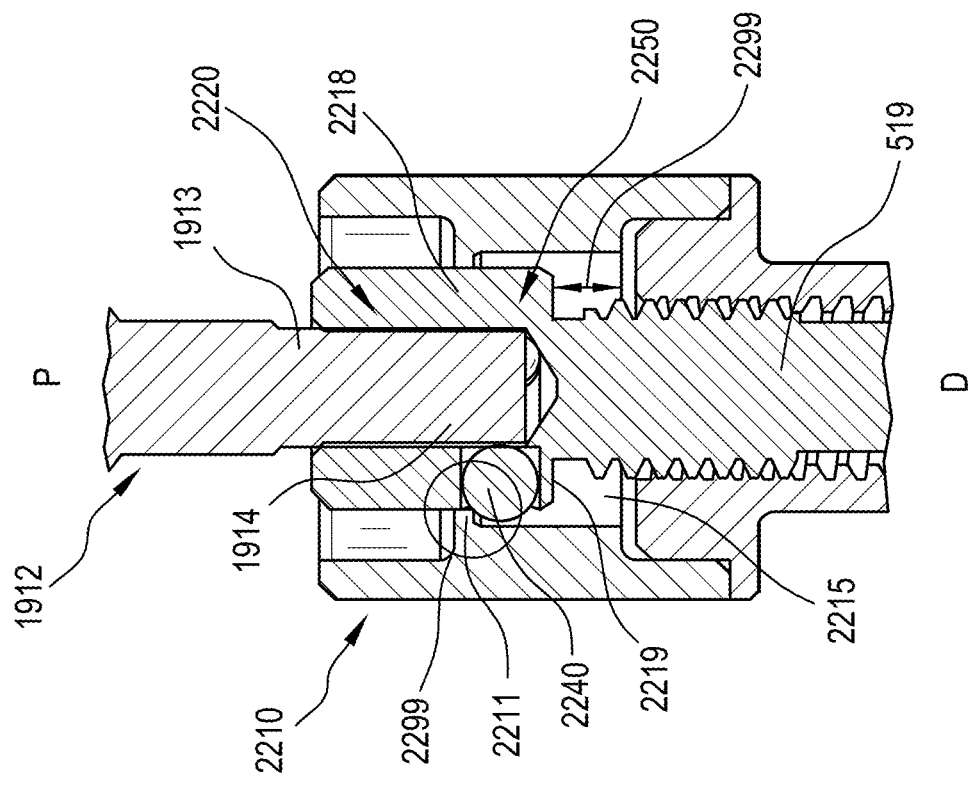
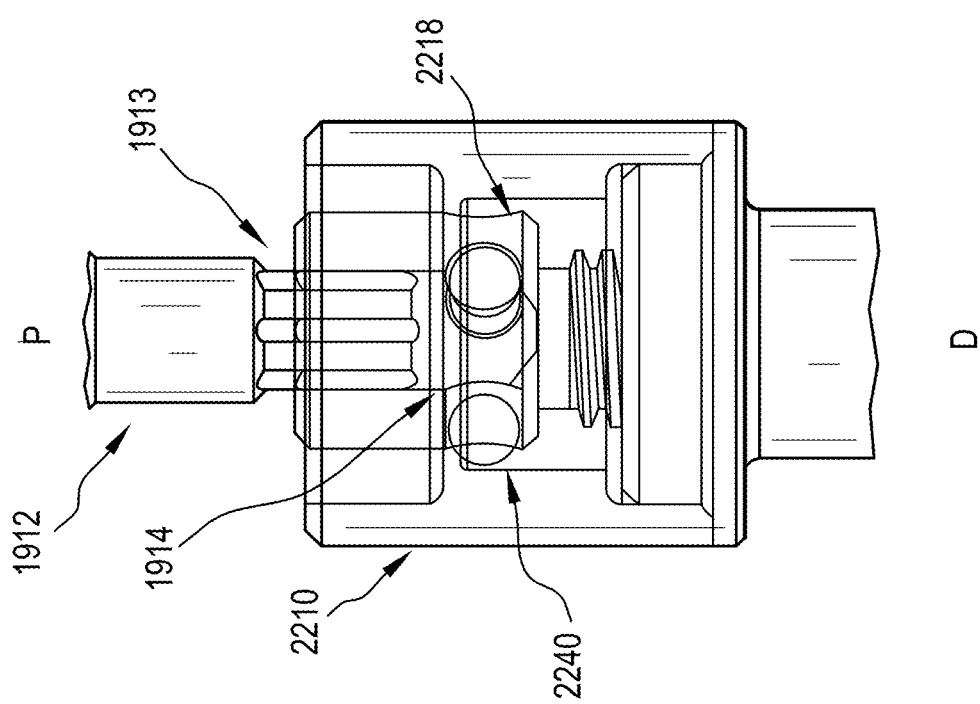

APPARATUS FOR DRIVER-SPECIFIC BACKOUT PREVENTION

FIELD

This disclosure relates generally to surgical instruments, systems, and methods, and more particularly to instruments, systems, and methods including a drive-specific backout prevention feature that selectively enables different drivers to operate a component. Such instruments, systems, and methods can be used in various procedures, e.g., orthopedic or neurologic surgical procedures such as spinal fusion surgery.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

Whether minimally invasive or not, there are a number of surgical procedures in which it can be desirable to form a working channel in a patient to provide access to a surgical site within the patient. One such example is orthopedic or neurologic surgical procedures, including, e.g., spinal fusion procedures where it can be desirable to form a working channel through a patient's tissue to access their vertebrae and/or the intervertebral discs disposed between adjacent vertebrae.

A variety of methods for providing such a working channel are known, including various devices that are anchored to a surgical table upon which a patient is disposed, devices that penetrate tissue without being anchored to any other structure, or devices that anchor to a plurality of anchors implanted in a patient's bone. In such arrangements, the devices may be inadequately supported, may undesirably move relative to a patient if the patient moves relative to the operating table or some other external structure, or may impede a surgeon or other user in performing some aspect of a procedure.

By way of example, in spinal procedures involving operation on a patient's intervertebral disc disposed between adjacent vertebrae, access to the disc space can be difficult. The advent of modular pedicle screws can allow pedicle anchors to be implanted before performing intervertebral disc operations. As a result, retractor assemblies are used to hold open a surgical access site for insertion of the pedicle screws and subsequent operation. However, retractor assemblies often require complex articulation of various retractor arms and blade to effectuate an optimized access site. Retractor devices therefore often use polyaxial joints that can be selectively loosened and tightened during a surgical procedure; however, retractor device components, including the polyaxial joint need to be disassembled and sterilized prior to and after use.

Accordingly, there is a need for improved devices, systems, and methods that ensure the safe and secure option of the locking mechanisms between instrumentation components to ensure that they are not accidentally disassembled during a surgical procedure, while also allowing selectable articulation and movement between certain components. For example, there is a need for improved fastener assemblies to allow multicomponent devices to be securely assembled and safely adjusted during a surgical procedure without risk of accidental disassembly.

SUMMARY

Surgical instruments, systems, and methods are disclosed herein that provide backout prevention for a screw used for polyaxial restraint and locking of components of surgical retractor assemblies. For example, the embodiments described herein provide a fastener and threaded housing assembly that can be used to adjust, for example, the position of a polyball in a socket of a polyaxial joint with two different drivers, where the first driver can be used to completely (e.g., back out) remove the fastener from the threaded housing, and the second driver can only be used to adjust the position of the fastener in the housing. The embodiments described herein can provide a number of advantages over prior approaches. This can include, for example, the ability to prevent accidental disassembly of the fastener from the housing during a surgical procedure when using a special driver trip for adjusting the fastener, the ability to insert and remove the fastener into the housing with a second driver before or after a surgical procedure in order to, for example, separately sterilize the fastener and housing.

A backout prevention mechanism includes a body configured to receive a fastener, the body defining a cavity configured to receive a head of the fastener when the fastener is disposed in the body, the cavity having an inwardly extending flange defining a proximal opening of the cavity, a fastener having a threaded portion and a head portion, and locking body disposed in each of the at least one radially extending channels of the screw. The head portion having an upper socket configured to interface with a driver for adjusting the position of the fastener within the body a lower socket, and at least one channel radially extending from the lower socket and sized and shaped to allow translation of a locking body through the channel. The backout prevention mechanism has a first configuration when the head portion of the fastener is engaged by a first driver and a second configuration when the head portion of the screw of engaged by a second driver. In the first configuration, engagement of a drive portion of the first driver with the upper socket of the head portion allows the locking body to move radially inward in the channel such that the fastener can be inserted distally into the body and removed proximally from the body without interference between the locking body and the flange of the cavity. In the second configuration, when the fastener is disposed in the body such that the at least one radially extending channel is disposed distal to the flange of the cavity, engagement of a drive portion of a second driver with the upper socket includes engagement of a distal end portion of the second driver with the lower socket of the head portion that displaces the locking body radially outward such that the locking body interferes with the flange of the channel when the fastener is advanced proximally by the second driver such that the fastener cannot be removed from the body by the second driver.

In some instances, the locking body is a ball bearing. The cavity can define a length below the flange, the length of the cavity defining a maximum possible adjustment distance for the fastener in the body in the second configuration. The cavity can define a cylindrical inner wall, and where the flange is a radial flange. In some instances, the inner wall of the cavity defines a width that is larger than a diameter of the head portion of the fastener plus twice an extension distance of the locking body from the head portion in the second configuration.

The radially extending channel is configured to retain the locking body in the radially extending direction. The lower socket can define cylindrical inner wall. The upper socket can define shape configured to interface with a shape of the drive portion of the first and second drivers and enable torque to be delivered from the drive portion to the fastener for adjusting the position of the faster in the body. The body can include a threaded portion configured to receive the threaded portion of the fastener.

In some instances, in the first configuration, a maximum engagement position of the drive portion of the first driver with the upper socket of the head portion is defined by contact between a drive shaft of the first driver and the upper socket, In some instances, in the second configuration, a maximum engagement position of the distal end portion of the second driver is defined by contact between the distal end portion and a bottom of the lower socket.

In some instances, in at least one of the first or second configurations, a maximum engagement position of the drive portion is defined by contact between drive features of the drive portion and an end of corresponding drive features in the upper socket.

Another example of the present disclosure is a surgical instrument having a retractor body configured to couple to an implantable anchor, a first tissue manipulating implement coupled to the retractor body and capable of polyaxial movement relative thereto, and a second tissue manipulating implement coupled to the retractor body and capable of polyaxial movement relative thereto. Each of the first and second tissue manipulating implements couples to the retractor body via a polyaxial joint, and each joint includes a screw to selectively lock the polyaxial joint against movement, and where each manipulating implement and screw includes a backout prevention mechanism according to example of the present disclosure, where the manipulating implant includes the body of the backout prevention mechanism and the screw includes the fastener.

In some instances, first and second tissue manipulating implements are opposed to one another such that they can move any of toward and away from one another.

The instrument can include a lock coupled to the body and configured to interface with the anchor extension to selectively lock a position of the body relative to the anchor extension.

In some instances, each of the first and second tissue manipulating implements couples to the body via a ball and socket joint. In some instances, each of the ball and socket joints includes an expanding member configured to selectively lock the ball and socket joint against movement.

Another example of the present disclosure is backout prevention system having a body configured to receive a fastener, the body defining a cavity configured to receive a head of the fastener when the fastener is disposed in the body, the cavity defining an inwardly extending flange at a proximal location of the cavity, a fastener having a threaded portion and a head portion having an upper socket configured to interface with a driver for adjusting the position of the fastener within the body, a lower socket, and at least one channel radially extending from the lower socket and sized and shaped to allow translation of a locking body through the channel. The system also includes a locking body disposed in each of the at least one radially extending channels of the screw and a locking driver having a distal end region sized and shaped to engage both the upper socket and lower socket, the distal end region having a drive portion and a locking portion located distal to the drive portion, where the drive portion is configured to interface with the upper socket for delivering torque to the fastener for adjusting the position of the fastener in the body, and here the locking portion is configured to be disposed in the lower socket when the drive portion is interfaced with the upper socket and is sized and shaped to displace the locking body radially outward to a position that prevents the locking body in the fastener from being moved proximally past the flange. Where a standard driver having a distal end having a drive portion without a locking portion sized and shaped to move the locking body radially outward is able to deliver a torque to the upper socket to adjust the position of fastener in the body proximally and distally without interference between the locking body and the flange.

In some instances, the body is a first body and the system further including a second body configured to couple to an implantable anchor, where the first body defines at least a portion of a manipulating implement configured to be connected to the second body and capable of polyaxial movement relative thereto, where the tissue manipulating implement couples to the second body via a polyaxial joint, and where the position of the fastener in the first body selectively locks the polyaxial joint against movement.

Yet another example of the present disclosure is method of assembling and adjusting the position of a fastener in a locking mechanism, the method including inserting the fastener into a body of the locking mechanism, coupling a first driver to the fastener and threading the fastener distally into engagement with the body using the first driver such that a locking body disposed in a radially extending channel of the fastener is disposed distal to an inwardly extending flange in a cavity of the body, with the fastener in threaded engagement with the body, coupling a second driver to the fastener, the second driver displacing the locking body radially outward such that the locking body interferes with the flange of the channel to prevent proximal movement of the fastener beyond a location where the locking body interfaces with the flange, adjusting the position of the fastener in the body using the second driver by threading the fastener between a maximum proximal location defined by the interference between the locking body and the flange and a maximum distal location. In some instances, the locking body is a ball bearing.

In some instances, the body includes a collet disposed in a socket, and wherein the inserting the fastener into the body includes coupling a distal end of the fastener to an expanding member disposed in the collet such that adjusting the position of the fastener in the body expands and contracts the collet in the socket and adjust a level of frictional engagement between the collet and the socket.

In some instances, the body is a first body that defines at least a portion of a manipulating implement and the socket is part of a second body that is configured to couple to an implantable anchor, and the method further includes coupling the collet to the socket after inserting the fastener to the first body with the first driver, the collet and socket defining a polyaxial joint, and wherein adjusting the position of the fastener in the body using the second driver includes selectively locking the polyaxial joint against movement.

Any of the features or variations described above can be applied to any particular aspect or embodiment of the present disclosure in a number of different combinations.

The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which:

FIG. 11A is a partially-transparent view of one embodiment of a driver-specific backout prevention assembly for use with the locking mechanisms of the polyaxial joints of the retractor of FIG. 2;

FIG. 11B is a cross-sectional view of the assembly of FIG. 11A showing the screw in a proximal position;

FIG. 11C is partially-transparent view of the assembly of FIG. 11A showing the screw in a distal position.

FIG. 11D is a cross-sectional view of the assembly of FIG. 11C;

FIG. 12A is a partially-transparent view of the driver-specific backout prevention assembly of FIGS. 11A-11D in use with the driver tip of FIG. 10B;

FIG. 12B is a cross-sectional view of the assembly of FIG. 12A showing the screw in a distal position with the backout prevention driver tip partially inserted;

FIG. 12E a partially-transparent view of the assembly of FIG. 12A showing the backout prevention driver tip fully inserted and the screw fully retracted and the backout-prevention mechanism engaging an inner flange of the body;

FIG. 12F is a cross-sectional view of the assembly of FIG. 12E;

DETAILED DESCRIPTION

Figure 1:
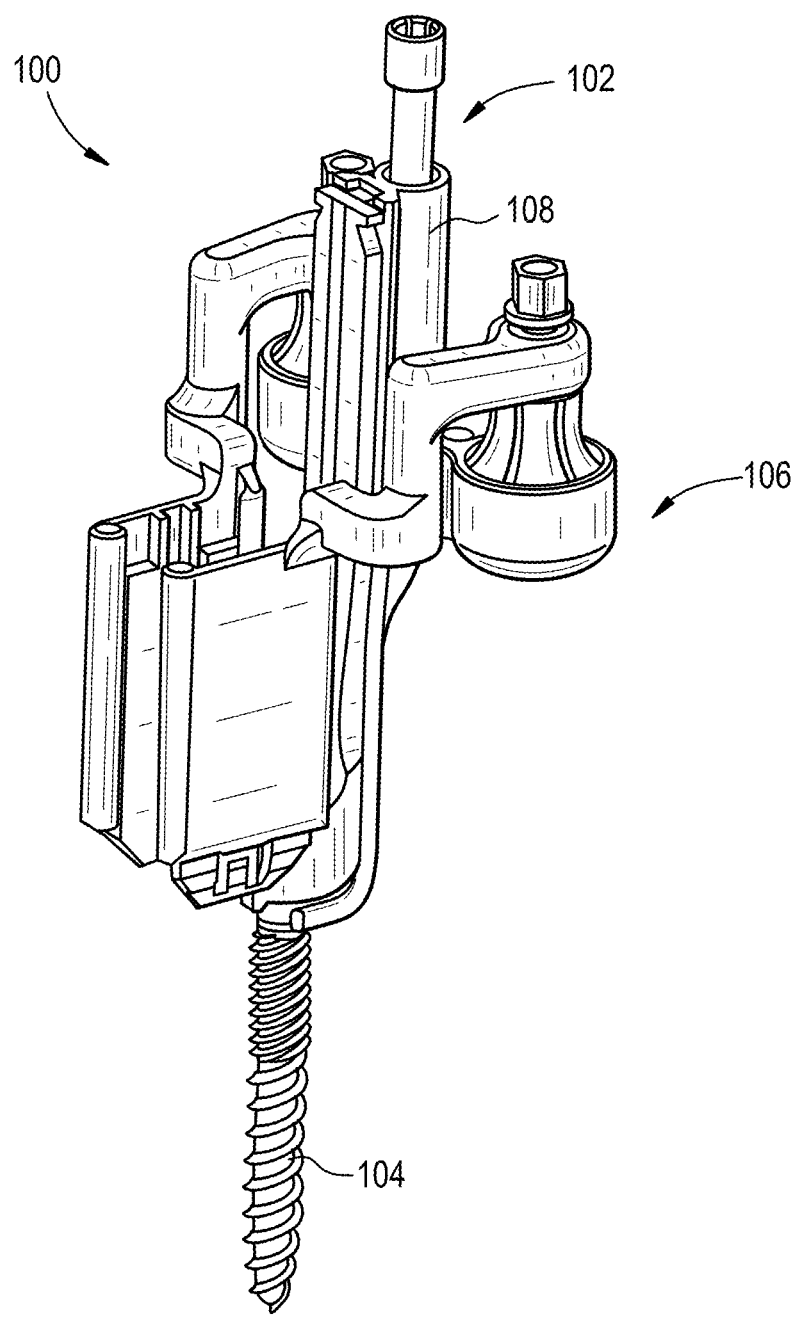
FIG. 1 is an illustration of one embodiment of a surgical instrument assembly according to the teachings provided herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

FIGS. 1-6 illustrate an exemplary surgical instrument assembly 100 according to the teachings provided herein. The assembly 100 can be used in various surgical procedures, including spinal surgeries such as microsurgical bone resection, spinal decompression, spinal fusion, and the like. In general, the assembly 100 can include a support instrument 102 that couples to an implanted anchor 104, such as a pedicle or other bone screw. The assembly 100 can further include a retractor 106 coupled to the support instrument 102. Other components not illustrated here can be included or coupled to the assembly 100. Such components can include, for example, any of a variety of cameras or visualization systems, and any of a variety of other surgical instruments.

An exemplary method of using the assembly 100 of FIGS. 1-6 can include any one or more of the following steps, performed in any of a variety of sequences: a) making an incision in a skin of a patient; b) percutaneously inserting through the incision an implantable anchor, such as a pedicle or other bone screw; c) coupling the support instrument 102 to the implanted anchor (e.g., a pedicle anchor); d) coupling a tissue retractor to the instrument; e) providing medial-lateral retraction of tissue surrounding an incision; f) coupling an optical visualization instrument to the tissue retractor and/or instrument; g) resecting a portion of the superior articular process, and/or performing a microsurgical decompression procedure; h) extracting intervertebral disc material including removing cartilaginous material from the vertebral endplates; i) inserting an interbody device; and j) deploying a mechanism of stabilization to stabilize the intervertebral segment.

The above described retractor assembly 106, in combination with the support instrument or anchor extension 102 and implanted anchor 104, can be used to, for example, widen an incision formed in a patient's skin and tissue to enable better access to a surgical site. By way of further example, in some embodiments these components can form an assembly that is anchored to a single implanted screw or anchor and provides medial-lateral tissue retraction to increase access for a variety of surgical procedures. Medially and laterally retracting skin and underlying tissue surrounding an incision can provide a wider opening and working channel between the tissue manipulating implements to access the patient's spine or intervertebral space. In some embodiments, the working channel can extend to encompass an adjacent anchor implanted in an adjacent vertebra. Once the tissue of the incision walls is retracted to form the working channel, any of a variety of surgical procedures can be performed by introducing one or more instruments through the working channel defined by the tissue manipulating implements of the retractor assembly. For example, procedures on the intervertebral disc space, such as disc replacement, discectomy, endplate preparation, fusion cage insertion, bone graft delivery, and the like can be performed by passing instruments or implants through the working channel.

Returning to FIGS. 1-6, FIG. 1 illustrates one embodiment of a surgical instrument assembly 100 that includes a support instrument 102 coupled to an implantable anchor 104 and a tissue retractor 106. Further details regarding embodiments of the assembly 100 can be found in U.S. application Ser. No. 16/139,409, entitled "PATIENT-MOUNTED SURGICAL SUPPORT," as well as U.S. application Ser. No. 16/139,434 entitled "PATIENT-MOUNTED SURGICAL RETRACTOR," both of which were filed on Sep. 24, 2018. Further details regarding embodiments of the implantable anchor 104 can be found in U.S. application Ser. No. 15/208,872, filed on Jul. 13, 2016, and entitled "BONE ANCHOR ASSEMBLIES AND RELATED INSTRUMENTATION." Furthermore, details regarding certain embodiments of retractors that can be used in the surgical assembly 100 can be found below and in U.S. Pat. No. 7,491,168. The entire contents of each of these references are incorporated by reference herein.

Figure 3:
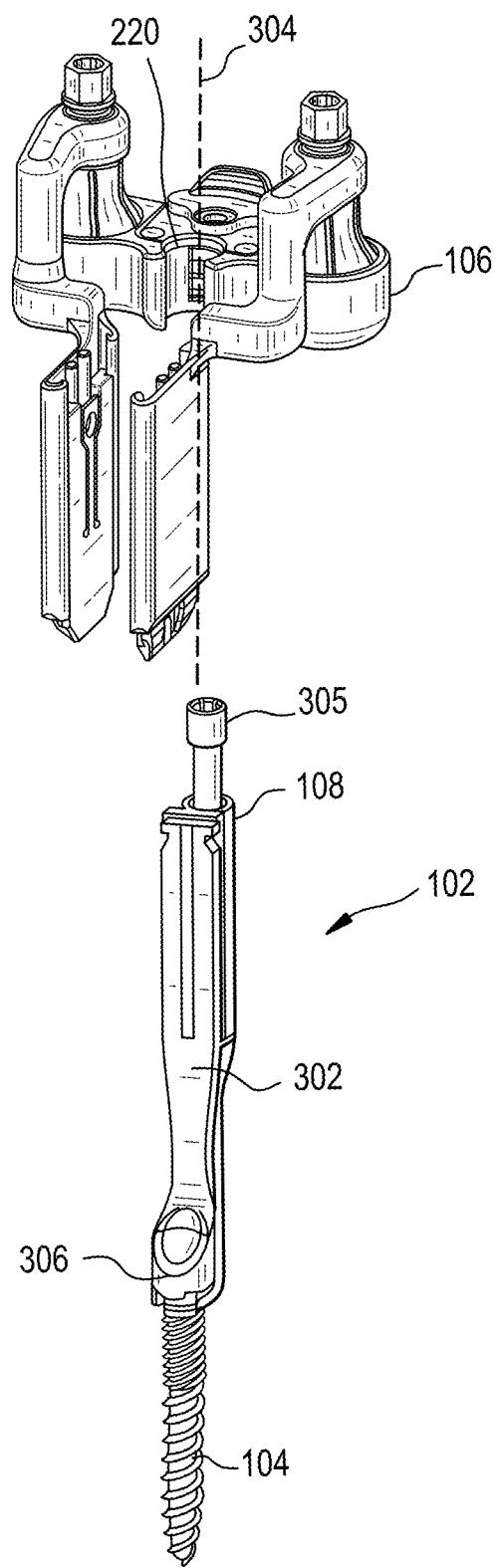
FIG. 3 is an exploded view of the assembly of FIG. 1.

Generally, the support instrument can include an elongate body 108 with a laterally-extending fork formed at a distal end thereof that can interface with a narrowed neck of the anchor 104. The fork can include opposed projections that extend laterally from a distal portion of the elongate body and define a U-shaped or otherwise open-ended recess that can be sized to receive a portion of the implantable anchor 104. For example, the projections can be configured to fit around a proximal portion of a bone anchor that can be part of a modular mono- or poly-axial pedicle screw. Such anchors can include a generally cylindrical distal shank portion with threads for tapping into bone, as well as a narrowed neck proximal of the shank portion and a wider proximal head. The proximal head can be generally spherical or semi-spherical in shape and can be configured to couple with a receiver head before or after implantation in a patient's bone. The elongate body can also include a lock configured to exert a drag force on the head of the anchor to control polyaxial movement of the instrument 102 relative to the anchor 104. As shown in FIG. 3, the lock can include a lock body 302 that is coupled to the elongate body 108 and translatable relative thereto along a longitudinal axis 304 of the elongate body. The lock body 302 can have a generally elongate shape to facilitate coupling with and translating or sliding along or relative to the elongate body 108. The lock can be actuated by a lock screw 305 that can cause distal translation of the lock body 302 as the screw is threaded further into the elongate body 108. The lock body 302 can further include a laterally-extending ring-shaped projection 306 at a distal end thereof that can be configured to contact the proximal head of the anchor 104 and exert a drag force thereon. The ring-shaped projection 306 can define a lumen to maintain access to a drive feature formed on a proximal end of the head of the anchor 104. This lumen, in combination with the lateral extension of the projection 306 and the fork formed at the distal end of the elongate body 108 can orient the instrument 100 such that a longitudinal axis of the instrument is laterally offset or non-coaxial with a longitudinal axis of the anchor 104. Such a configuration can allow a driver or other instrument to access the drive feature of the anchor 104 even when the instrument 100 is coupled thereto. This can enable flexibility to implant the anchor 104 any of before and after coupling the instrument 100 thereto.

Returning to FIG. 2, a more detailed illustration of one embodiment of the tissue retractor 106 is provided. The retractor 106 can include a body 202 that can be configured to couple to the support instrument or anchor extension 102. First and second tissue manipulating implements 204, 206 can be coupled to the body 202 by, for example, rigid arms 208, 210, respectively. Each of the first and second tissue manipulating implements 204, 206 can be capable of polyaxial movement relative to the body via a polyaxial joint 212, 214, such as a ball-and-socket joint. Such a joint can allow the tissue manipulating implements 204, 206 to move relative to one another in a variety of manners. For example, the implements 204, 206 can be pivoted toward or away from one another about an axis extending parallel to a longitudinal axis of a support instrument 102, (e.g., an axis parallel to the axis 304 in FIG. 3). The implements 204, 206 can also be pivoted toward or away from one another about an axis transverse or oblique to, e.g., the axis 304. For example, the implements 204, 206 can be toed relative to one another, wherein distal ends of the implements are moved toward or away from one another by an amount greater than proximal ends of the implements. In some embodiments, toeing can include moving distal ends of the implements away from one another while proximal ends of the implements are either moved toward one another or do not move such that a distance between the proximal ends of the implements remains unchanged. Furthermore, each polyaxial joint 212, 214 can include a lock 216, 218 that can be used to selectively lock a position of the associated tissue manipulating implement 204, 206 or impose a drag force to inhibit movement in the absence of at least a threshold level of force.

Figure 2:
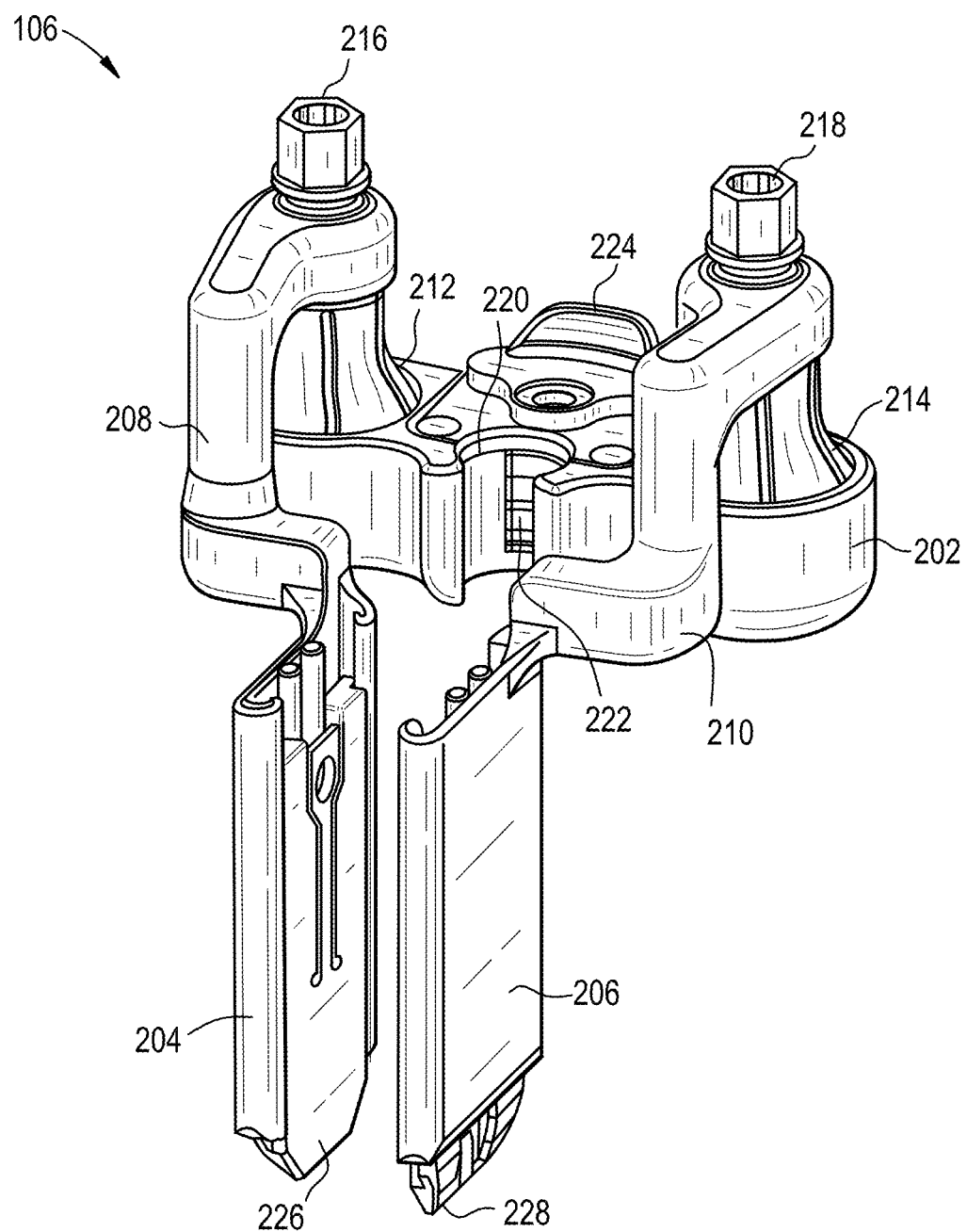
FIG. 2 is a detail view of a retractor of the assembly of FIG. 1.

As noted above, the tissue retractor 106 can be configured to couple to a support instrument or anchor extension 102 and can be configured to slide along a length of such an instrument to adjust a height of the retractor relative to the implanted anchor 104. As shown in FIG. 2, the body 202 of the retractor can include a closed or partially-open lumen or recess 220 configured to receive a portion of the support instrument 102, such as a generally cylindrical elongate body 108 (see FIG. 1). The retractor 106 can further include a feature to selectively lock a position of the retractor relative to the support instrument 102, such as a spring-biased protrusion or pawl 222 that can engage a ratchet rack or other series of recesses or other surface features formed on the elongate body 108 of the support instrument. Furthermore, in some embodiments the locking feature 222 can be configured to prevent not only movement along a length of the support instrument 102, but also rotation thereabout. An actuator 224, such as the illustrated sliding or translating member, can be included to allow a user to easily withdraw the protrusion 222 against the biasing force of a spring or other biasing element disposed within the body 202 of the retractor 106.

In addition to adjusting a position of the retractor 106 along a length of the support instrument 102, a length of each of the tissue manipulating implements 204, 206 can also be adjusted. For example, in some embodiments the tissue manipulating implements 204, 206 can each include an extension 226, 228 that can be configured to translate relative to the tissue manipulating implements 204, 206. Proximally or distally translating either extension 226, 228 relative to the associated implement 204, 206 can change an overall length of the implement and, for example, can allow an implement to reach deeper into tissue even if the retractor 106 is mounted at a greater height above a patient's skin surface along a more proximal portion of the support instrument elongate body 108.

FIG. 3 illustrates a partially exploded view showing how the retractor 106 can be coupled to the support instrument 102 by sliding the retractor down or distally over a proximal portion of the support instrument. For example, the recess or lumen 220 of the retractor 106 can be aligned with the generally cylindrical elongate body 108 of the support instrument and the retractor can be advanced down or distally along the axis 304. While advancing the retractor relative to the support instrument, a user can manually retract the spring biased pawl or protrusion 222 using the sliding lever 224 to allow free movement of the retractor relative to the support instrument. When a desired position is reached, the user can release the lever 224 such that the protrusion 222 is advanced into engagement with a complementary recess or other feature formed on the elongate body 108 to maintain the relative positioning of the retractor and support instrument. In other embodiments, the complementary features formed on the elongate body 108 and the protrusion 222 can be formed as a biased ratchet wherein, e.g., distal advancement of the retractor can be achieved without actuating the lever 224, but proximal withdrawal of the retractor 106 relative to the instrument 102 requires actuating the lever 224 to withdraw the biased protrusion 222.

Figure 4:
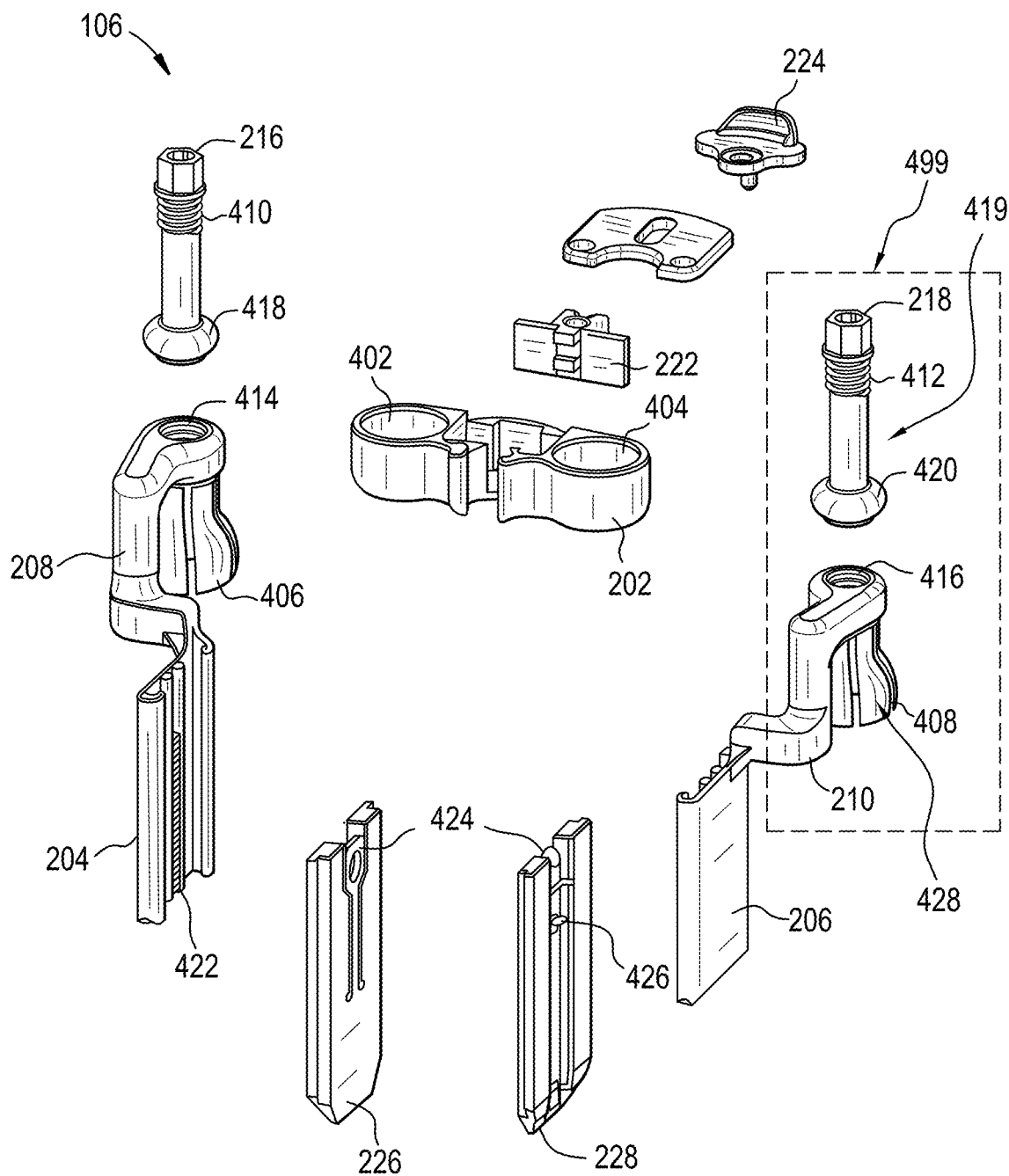
FIG. 4 is an exploded view of the retractor of FIG. 2.
Figure 5:
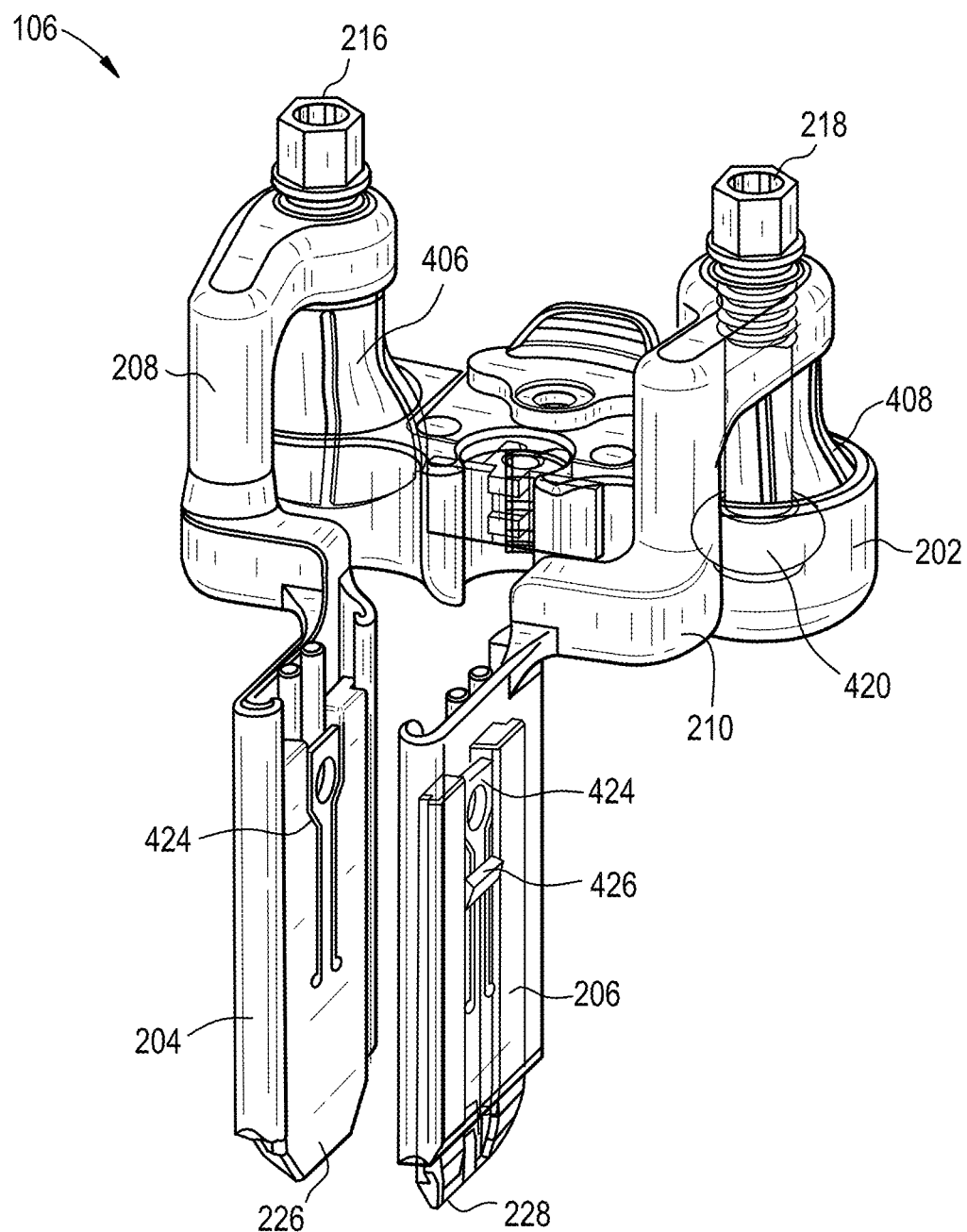
FIG. 5 is a partially-transparent detail view of the retractor of FIG. 2.
Figure 6:
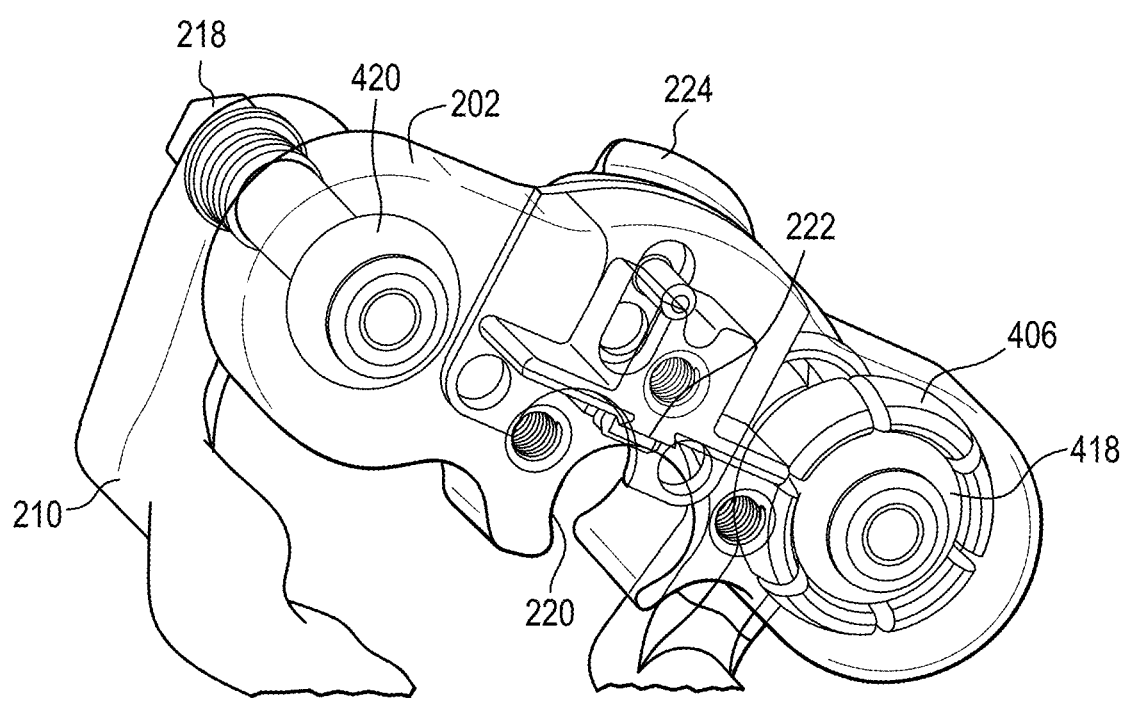
FIG. 6 is a bottom partially-transparent detail view of the retractor of FIG. 2.

FIGS. 4-6 illustrate the retractor 106 in various exploded and partially transparent views to better explain the interaction of various components thereof. For example, the polyaxial joints 212, 214 can be seen in greater detail. Each polyaxial joint 212, 214 can include a socket 402, 404 formed in the body 202 of the retractor 106. Each of the arms 208, 210 coupled to the tissue manipulating implements 204, 206 can have a generally ball-shaped proximal end 406, 408 (e.g., a collet) that includes one or more relief slots formed therein such that various portions of the proximal end (e.g., petals 428) can deform relative to other portions thereof. A lock 216, 218 can be coupled to each arm 208, 210 by cooperation between threads 410, 412 formed on the lock and threads 414, 416 formed on an inner surface of through-holes in the arms 208, 210. Further, an expanding member 420 can be disposed at a distal end of each lock 216, 218 and arranged within the ball-shaped proximal end 408 such that adjustment of the lock 218 position by movement along the threads 412 can move the expanding member 420 distally within the ball-shaped proximal end 408 such that it urges the petals 428 outward or the expanding member 420 can be retracted proximally such that it sits more in a curved inside surface of the petals 408 and does not urge them outward. A lock assembly 499 can include a lock 218 and a portion of the arm 210 to which the lock 218 is operatively coupled.

When assembled, as shown in FIGS. 5 and 6, the expanding members 418, 420 can be disposed within the generally ball-shaped proximal ends 406, 408 in an un-locked (e.g., retracted) position that allows the expanding members 418, 420 to be disposed within one of the sockets 402, 404 of the body 202. To lock the ball-shaped proximal ends 406, 5408 within and relative to one of the sockets 402, 404, the locks 216, 218 can be rotated relative to the arms 208, 210 to advance the expanding member 420 farther into the ball-shaped proximal end 408 due to the threaded coupling between the arms 208, 210 and the locks 216, 218. Advancement of the locks 216, 218 into the ball-shaped proximal end 408 can cause the expanding member 418, 420 formed at a distal end of each lock to expand the petals 428 radially outward inside the sockets 402, 404. As the petals 428 of the ball-shaped proximal ends 406, 408 expand radially, they are urged into contact with the sidewalls of the sockets 402, 404. This can cause an increase in frictional force between the sockets 402, 404 and the ball-shaped proximal ends 406, 408 of the arms 208, 210. Further, upon sufficient advancement of the locks 216, 218, the force of the expanding members 418, 420 against the petals 428 can effectively lock the ball-shaped proximal ends 406, 408 in a given position and thereby prevent any movement of the arms 208, 210 or tissue manipulating implements 204, 206 coupled thereto.

Figure 7:
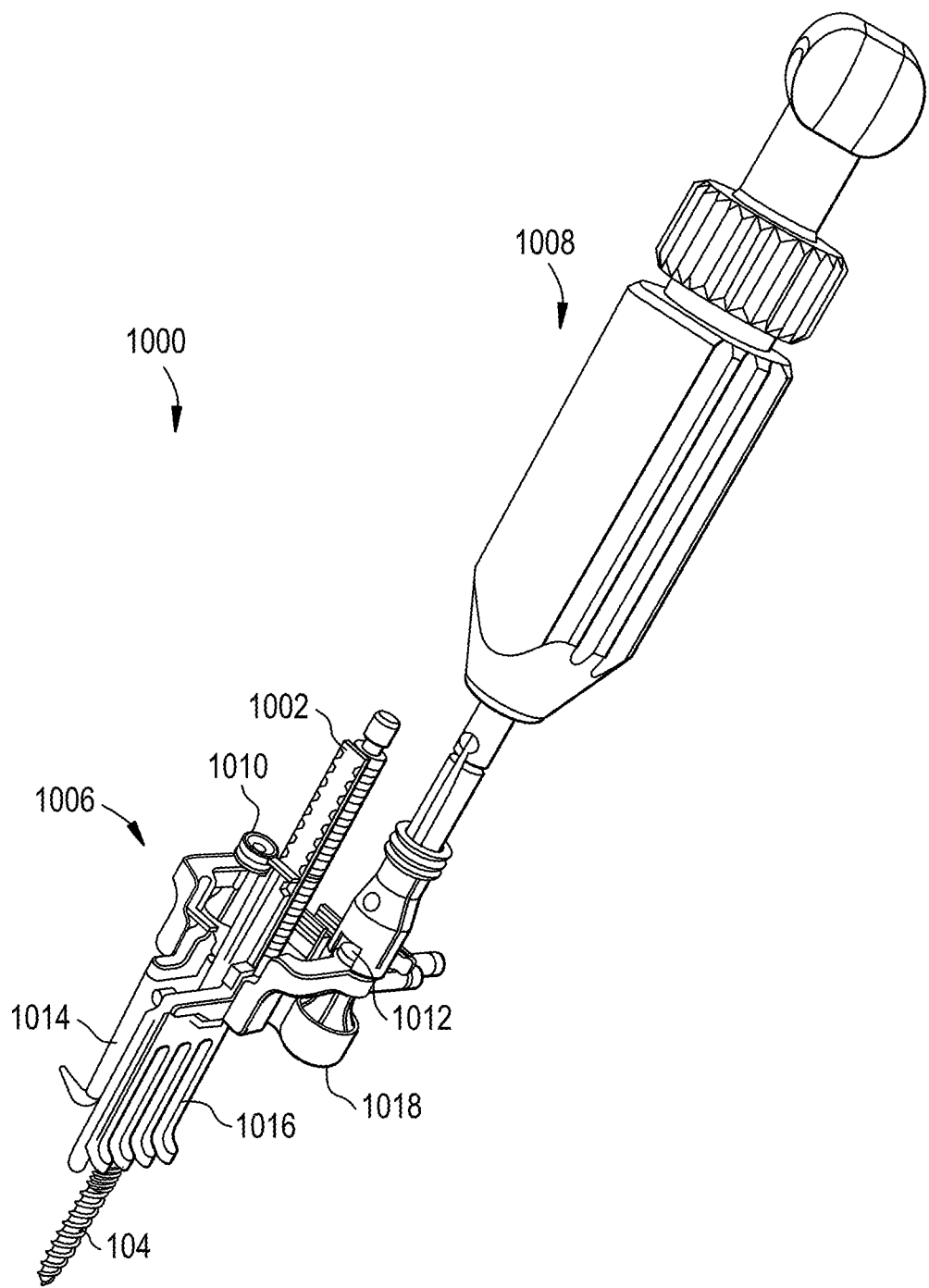
FIG. 7 is a front perspective view of another embodiment of a surgical instrument assembly according to the teachings provided herein.

FIG. 7 illustrates an alternative embodiment of a surgical instrument assembly 1000 that includes a support instrument 1002 coupled to an implantable anchor 104 and a tissue retraction assembly 1006. Also shown is an embodiment of a driver 1008 that can be used to actuate locks 1010, 1012 that can selectively permit or prevent polyaxial movement of opposed tissue manipulating implements 1014, 1016 relative to a body 1018 of the retraction assembly 1006.

Figure 8A:
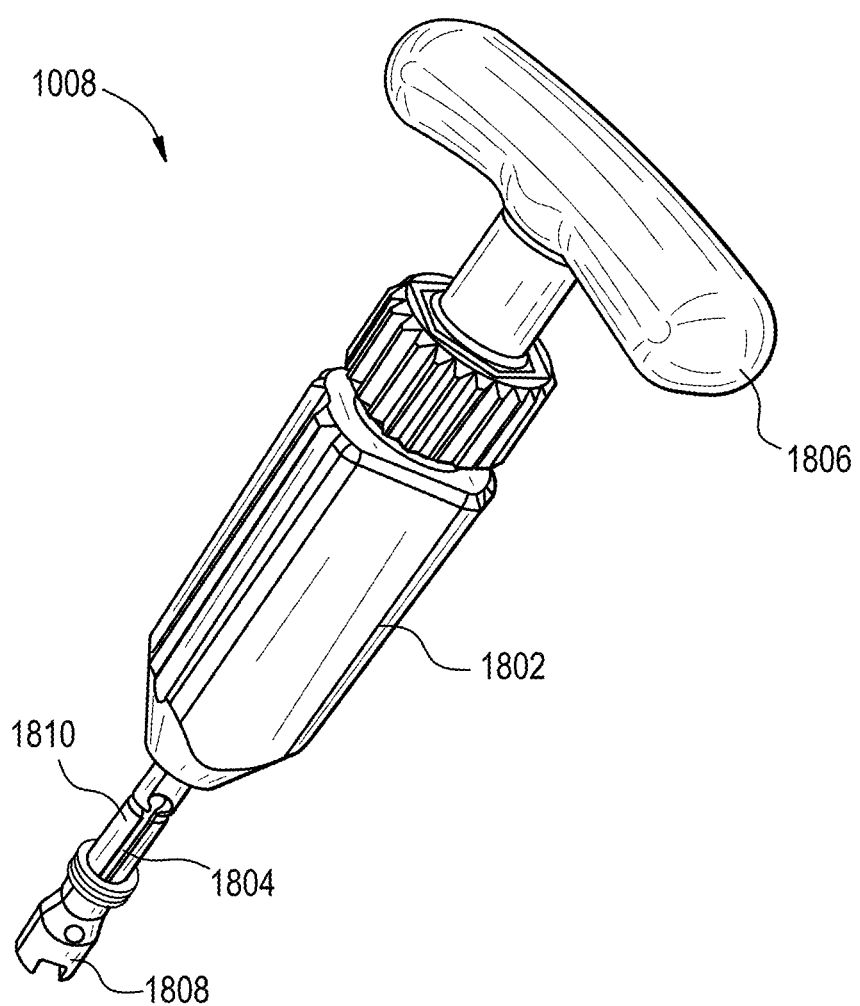
FIG. 8A is a perspective view of an actuating instrument of the assembly of FIG. 7.
Figure 8B:
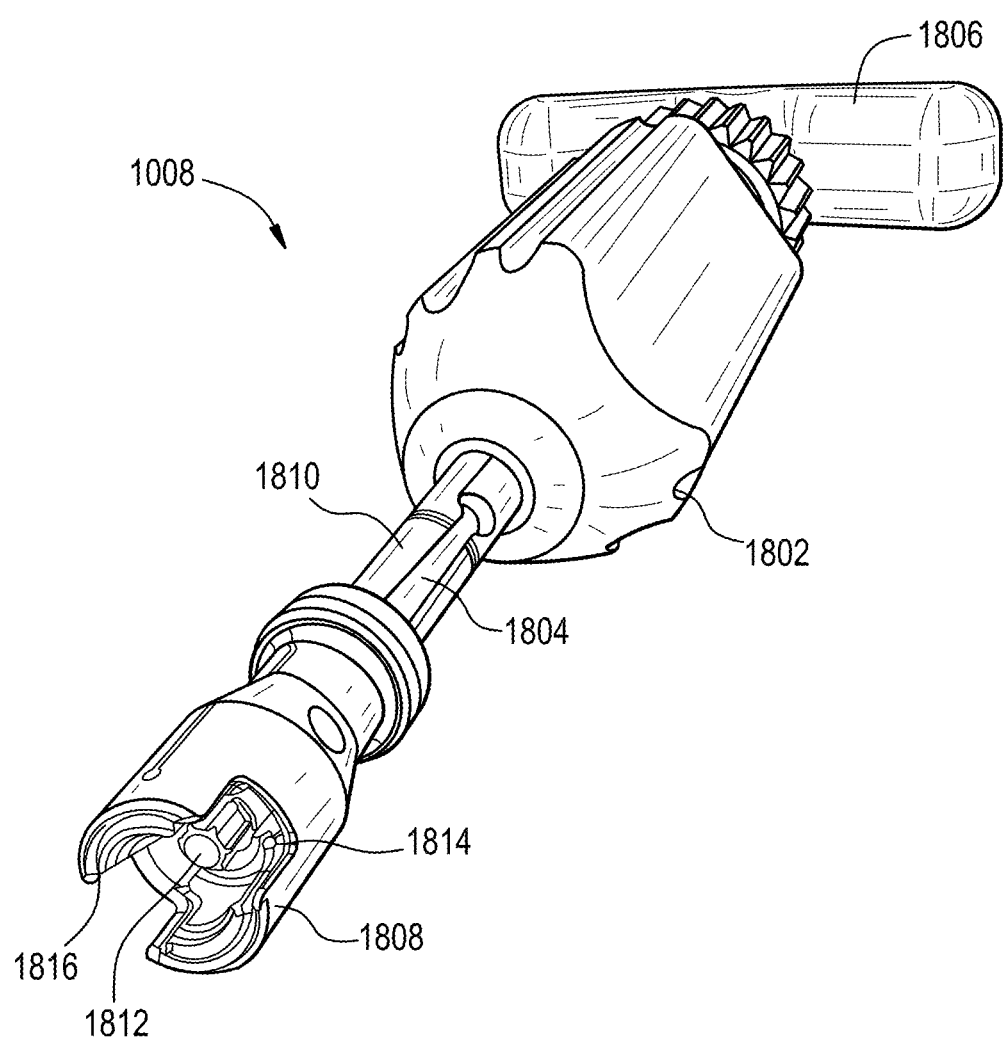
FIG. 8B is an alternative view of the actuating instrument of FIG. 8A.
Figure 9:
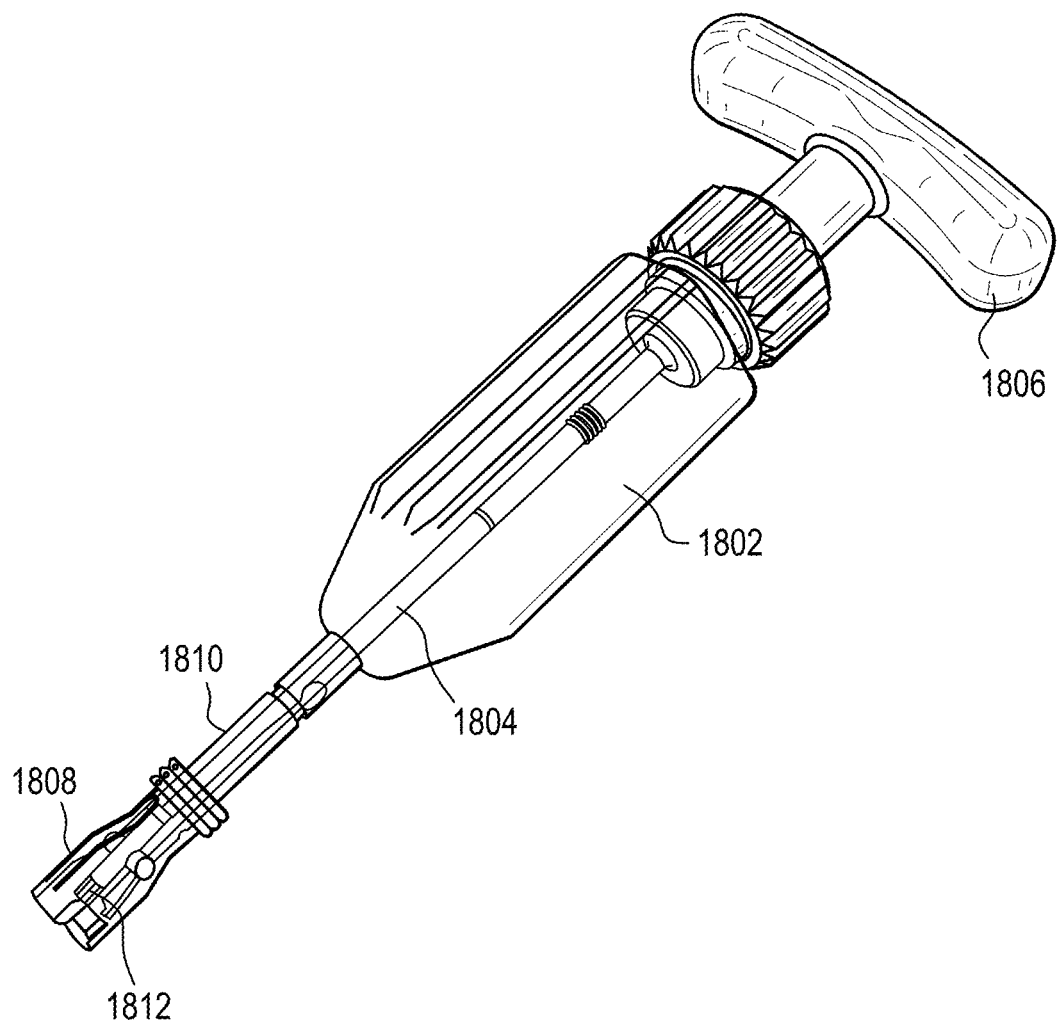
FIG. 9 is a partially-transparent perspective view of the actuating instrument of FIG. 8A.

FIGS. 8A-9 illustrate the driver 1008 in greater detail. In some embodiments, the driver 1008 can include a housing 1802 disposed about a driveshaft 1804 that couples to a handle 1806 at a proximal end thereof. A distal end 1812 of the driveshaft 1804 can be configured to interface with a proximal end of a lock 1010, 1012 of the tissue retractor assembly 1006 to impart an actuating torque thereto. The driver 1008 can also include a stabilizing shaft 1810 disposed coaxially about the driveshaft 1804 and coupled to the housing 1802 and an interface 1808. The interface 1808 can include opposed slots or cut-outs 1814, 1816 that can receive portions of one of the arms 1302, 1304 when the interface is disposed over one of the locks 1010, 1012 such that the distal end 1812 of the driveshaft 1804 engages the lock. A user can then counter brace against any tendency of the retractor assembly 1006 to rotate or otherwise move in response to turning the handle 1806 by holding the housing 1802 steady. More particularly, the rigid, non-rotational coupling between the housing 1802, the stabilizing shaft 1810, and the interface 1808, in combination with the interface 1808 being unable to rotate relative to the arms 1302, 1304 due to the slots 1814, 1816, can provide effective stabilization when a user holds the base 1802 while turning the handle 1806.

One issue encountered with instruments of the type described above is that a user might unintentionally back the screw 419 of the lock 216, 218 out too far during a procedure. This can cause the screw 419 to become decoupled from the threads 414, 416 of the tissue manipulating implement arms 208, 210. In order to prevent this, embodiments of the present disclosure provide a mechanism to stop the screw 419 of the lock, 216, 218, which is also referred to as a polyball tightening screw, from being unintentionally removed during a procedure. However, because the screw 419 also needs to be disassembled for cleaning and initial assembly, the screw 419 needs to be selectively removable past its backstop. Therefore, a back-out prevention mechanism allowing for selective removal of the screw 419 past a backstop is provided and described herein. This mechanism can be added to the lock assembly 499, where backing out of the screw 419 is necessary to allow collapse and insertion of the petals 428 of the ball shaped proximal end 408 into the socket 404, however backing out completely disconnects the screw 419 from the from the threads 416 and/or the expanding member 420. This creates the need for a backstop to inform the user when the screw 419 is sufficiently backed out and/or prevent an unintended disconnection of the screw 419 from the expanding member 420 while still allowing adjustment of the screw 419 to enable adjustment of the lock assembly 499.

One purpose of the back-out prevention mechanism is to allow backout prevention to occur without permanently capturing the screw or lock 218, since permanent capture of the screw of the lock 218 is undesirable due to challenges posed when sterilizing components. For example, the assembly 499 may need to be completely disassembled after use and each component fully sterilized, which would require both decoupling the screw 419 from the threads 416 and the expanding member 420 from the screw 419. If a more traditional captured screw was utilized to prevent unintentional backout, full disassembly would not be possible and thorough cleaning and sterilization can be difficult. Accordingly, the present disclosure provides a mechanism for selective backout prevention based on the driver utilized by a user, which can permit selective prevention of backout during a procedure but allow complete disassembly for cleaning and sterilization. As explained in more detail below, the lock assembly 499 can include a fastener (e.g., a screw 419) and a body (e.g., a portion of the arm 210 receiving the screw 419) that operate together to provide a back-out prevention mechanism that enables the screw 419 to be assembled or disassembled or adjusted with a first driver, and adjusted with a second driver, where the second driver cannot be used to disassemble or back-out the screw 419 from the arm 210.

Figure 10A:
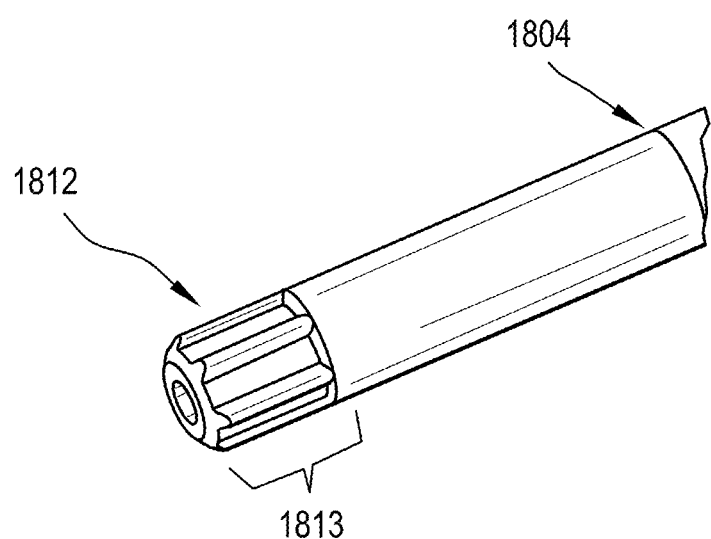
FIG. 10A is a perspective view of the distal end driver tip of the actuating instrument of the assembly of FIG. 7.
Figure 10B:
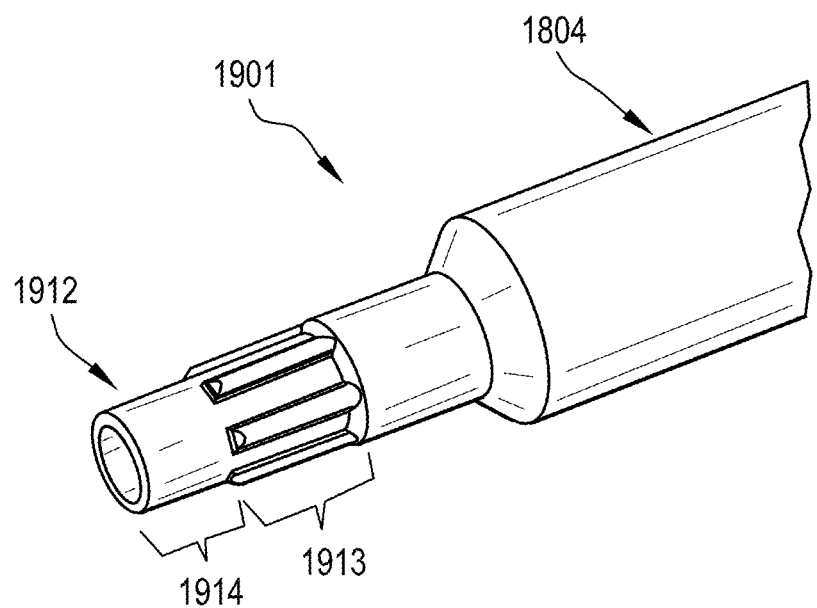
FIG. 10B is a perspective view of an alternative distal end driver tip for use with the actuating instrument of the assembly of FIG. 7.

FIG. 10A is a perspective view of one embodiment of a distal end 1812 driver tip 1813 that can be utilized on, for example, the actuating instrument 1008 of the assembly of FIG. 7. The arrangement of FIG. 10A can also be referred to as a standard driver. As explained in more detail below, the standard driver 1812 can be used to fully adjust the positioning of the lock 218 or other fastener in a lock assembly 499 (or the lock assembly 599 as shown in FIGS. 11A-14), including an initial assembly or subsequently disassembly of the lock assembly 499. FIG. 10B is a perspective view of an alternative distal end driver tip for use with the actuating instrument of the assembly of FIG. 7. FIG. 10B shows a backout prevention driver 1901 that includes a distal end 1912 with two separate regions: a proximal driver tip 1913 and a distal interference element 1914 extending between the driver tip 1913 and the termination of the distal end 1912. In operation, and as discussed in more detail below, use of the backout prevention driver 1901 with the lock assembly 499, 599 prevents the fastener or lock 218 from being disassembled or completely backed-out from the body 210.

In FIGS. 10A and 10B, the driver tips 1813, 1913 are illustrated as having hexlobe drive features, which are one of many common driver features and are only shown as an example. Many different driver features can be used with the examples disclosed herein.

FIGS. 11A-11D are partially-transparent and cross-sectional views of a driver-specific backout prevention assembly 599 for use with the screw 419 and lock 218 of the polyaxial joints of the retractor of FIG. 2. FIG. 11A is a partially-transparent view and FIG. 11B is a cross-sectional view, both showing the driver-specific backout prevention assembly 599 with a standard driver 1812 disposed in a socket 2218 of a screw 519 that is disposed in a body 2210. The body 2210 can be, for example, the portion of the arm 210 receiving the screw 519. The screw 519 can have a threaded portion that is threaded into a corresponding threaded portion of the body 2210. In some instances, however, the body 2210 and the portion having the corresponding threading 416 can be separate parts and, in yet other examples, the screw 519 and the body 2210 can be connected with a means other than threading, such as a pin and channel system or other means known in the art. Continuing, the body 2210 defines a cavity 2215 for receiving the head portion 2218 or socket of the screw 519. The cavity 2215 includes an inwardly extending flange 2211 or protrusion that serves as a back stop when a backout prevention driver is disposed in the head portion 2218 (as illustrated in FIGS. 12A-12H).

Returning to FIGS. 11A and 11B, the head portion of the screw 419 defines an upper socket 2220 and a lower socket 2250, with the drive tip 1813 only being able to engage the upper socket 2220. The head portion 2218 also includes one or more channels 2219 that extend radially from the lower socket 2250. Each channel 2219 containing a locking body, such as the ball bearing 2240 shown. In operation, the backout prevention assembly 599 allows the standard driver 1812 to completely insert and remove the screw 519 from the body 2210 because the ball bearings 2240 disposed in the channels 2219 do not interfere with the flange 2211, due to their ability to be deflected radially inward by the flange 2211 at least partially into the lower socket 2250, as illustrated. Accordingly, FIGS. 11A and 11B show the backout prevention assembly 599 in an "up" position with a standard driver 1812, where the male hexlobe feature of the driver tip 1813 has bottomed out on the female lobes in the upper socket 2220 and the ball bearings 2240 are free to move inwards and allow removal of the screw 519 from the body 2210. FIGS. 11C and 11D show the backout prevention assembly 599 in a "down" position with the standard driver 1812. Additionally, distal advancement of the screw 419 is limited by the interaction of the distal facing surface of the head portion 2218 with a proximal facing surface of the cavity, as illustrated in FIG. 11D.

Figure 12C:
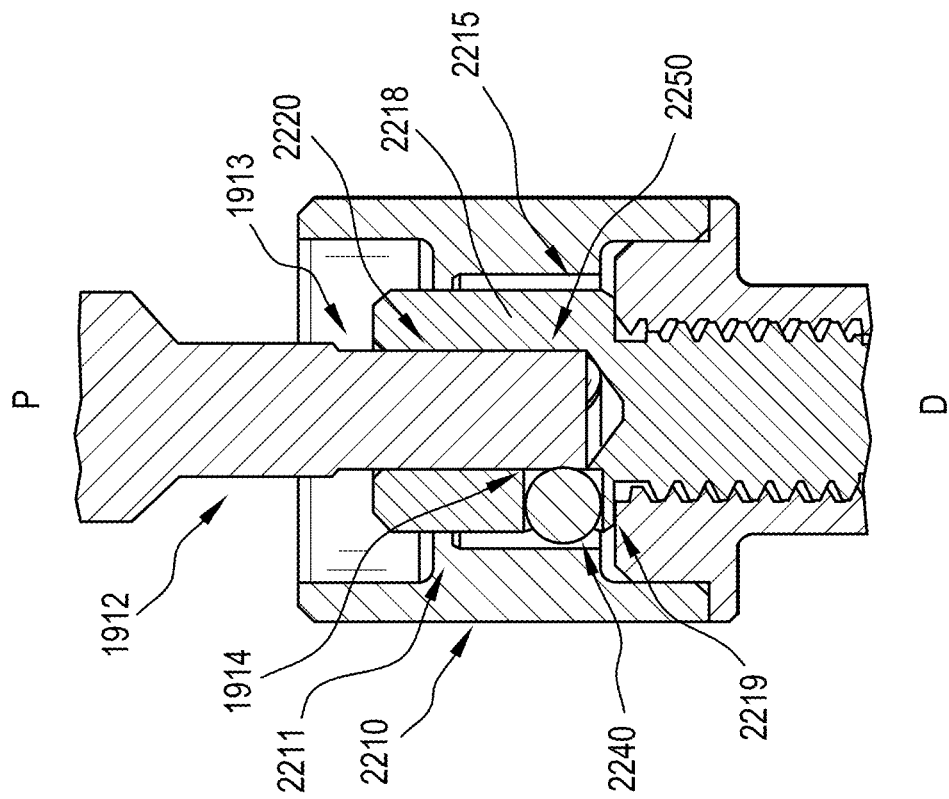
FIG. 12C is a partially-transparent view of the assembly of FIG. 12A showing the backout prevention driver tip fully inserted.

FIGS. 12A-H are partially-transparent and cross-sectional views of the driver-specific backout prevention assembly 599 of FIGS. 11A-11D in use with the backout prevention driver 1901 of FIG. 10B. FIGS. 12A and 12B show the insertion of the distal end 1912 of the backout prevention driver 1901 into the head portion 2218 of the screw, where the screw 519 is the "down" position and the interference element 1914 is disposed in the upper socket 2220. In this position, the interference element 1914 cannot engage the upper socket 2220 to drive the screw 519, as the interference element 1914 lacks engagement features. Additionally, the ball bearings 2240 are not restricted by the anything disposed in the lower socket 2250 and are free to move.

Figure 12D:
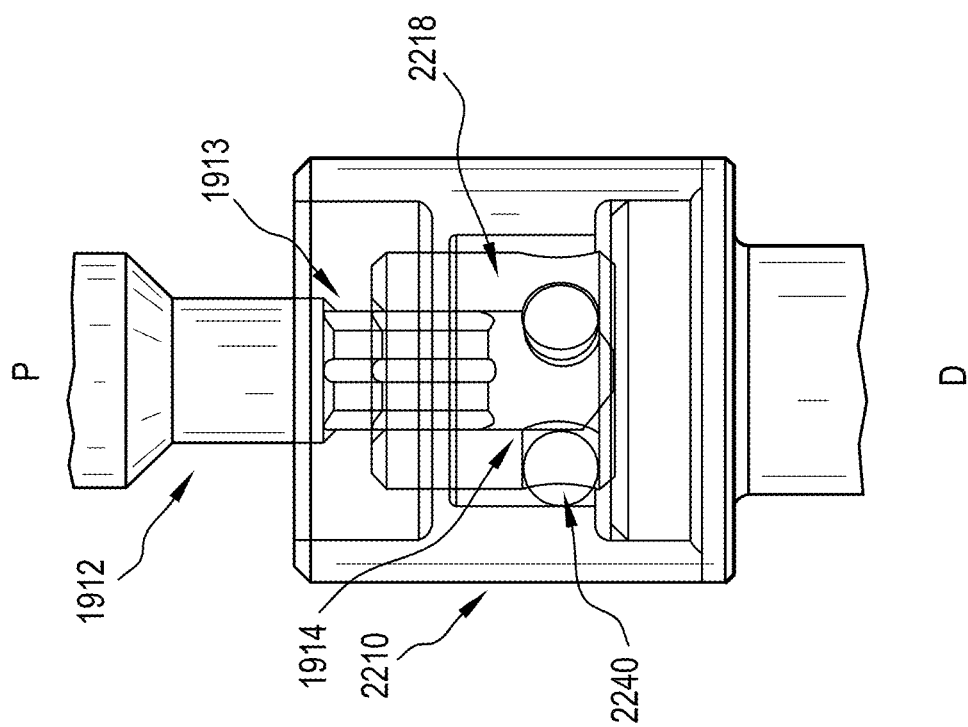
FIG. 12D is a cross-sectional view of the assembly of FIG. 12C.

Complete insertion of the distal interference element 1914 into the lower socket 2250 is shown in FIGS. 12C and 12D, where the features of the driver 1913 (e.g., male hexlobe) have bottomed out on the corresponding features (e.g., female lobes) of the upper socket 2220, and the interference element 1914 is disposed in the lower socket 2250. Due to the presence of the interference element 1914, the ball bearings 2240 are displaced radially outward until they extend from the head portion 2218 and into the cavity 2215 of the body 2210. The ball bearings 2240 extend from the head portion beyond the outer diameter of the head portion and to a distance where they interfere with the flange 2211 as the screw 519 is driven proximally, as shown in FIGS. 12E and 12F.

In FIGS. 12E and 12F, the backout prevention driver 1901 has been used to back the screw 519 out of the body 2210 until the ball bearings 2240 reach an interference position (indicated by circle 2299) with the flange 2211. Because the presence of the interference element 1914 in the lower socket 2250 prevents the ball bearings 2240 from moving radially inward past the inner diameter of the flange 2211, the backout prevention driver 1901 cannot back the screw 519 out past the position shown. Accordingly, once the screw 519 is disposed in the body 2210 with the channel 2219 past the flange 2211, the backout prevention driver 1901 can only be used to adjust the position of the screw 519 as allowed by the length 2299 of the cavity 2215 below the head portion 2218 when the locking ball bearing 2240 abuts the flange 2211.

Figure 12H:
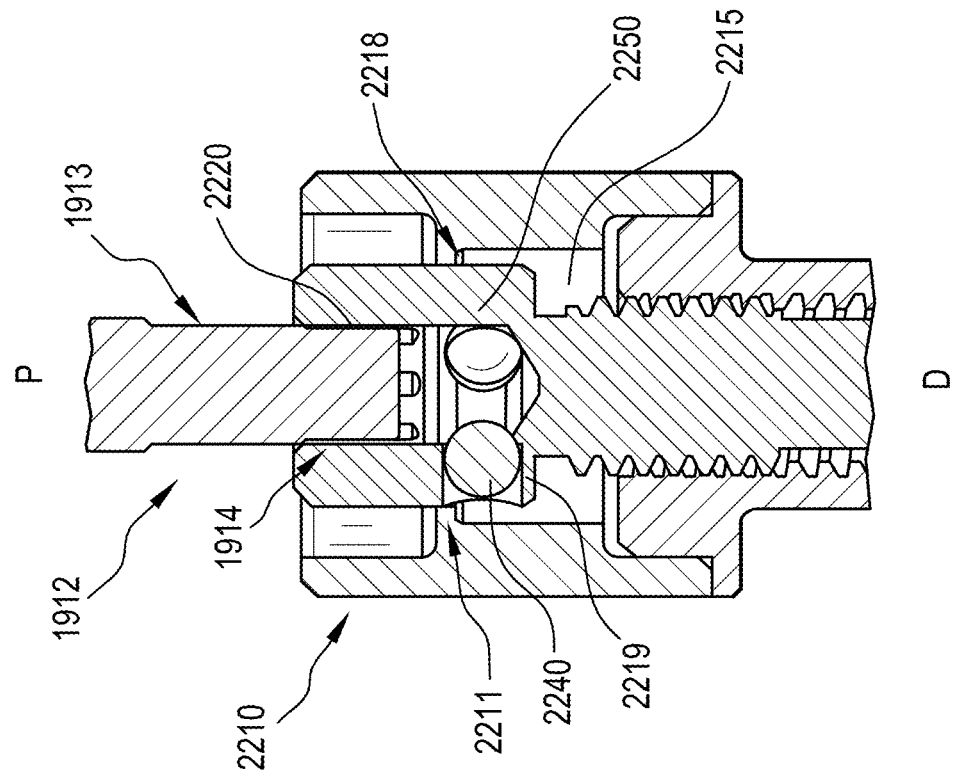
FIG. 12H is a cross-sectional view of the assembly of FIG. 12G.
Figure 12G:
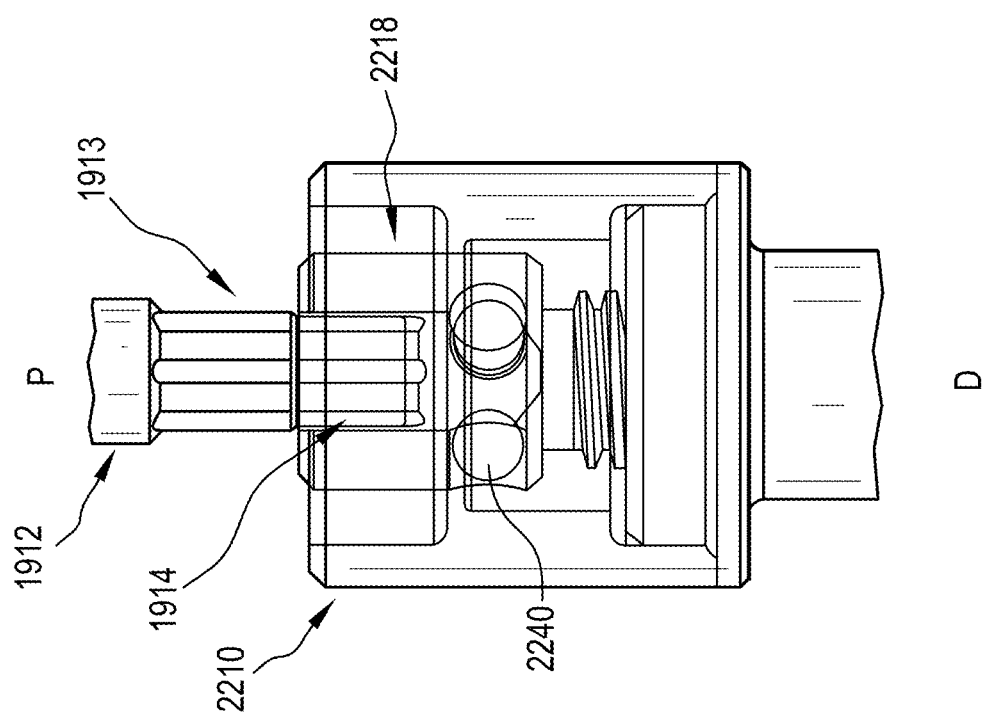
FIG. 12G is a cross-sectional view of the assembly of FIG. 12A showing the screw in a proximal position with the backout prevention driver tip partially inserted.

FIGS. 12G and 12H illustrate removal of the backout prevention driver 1901 from the head portion 2218, whereby the ball bearings are free to move radially inward into the lower socket 2250, thereby allowing the screw 519 to be retracted proximally past the flange 2211 using, e.g., the standard driver 1812.

Figure 13A:
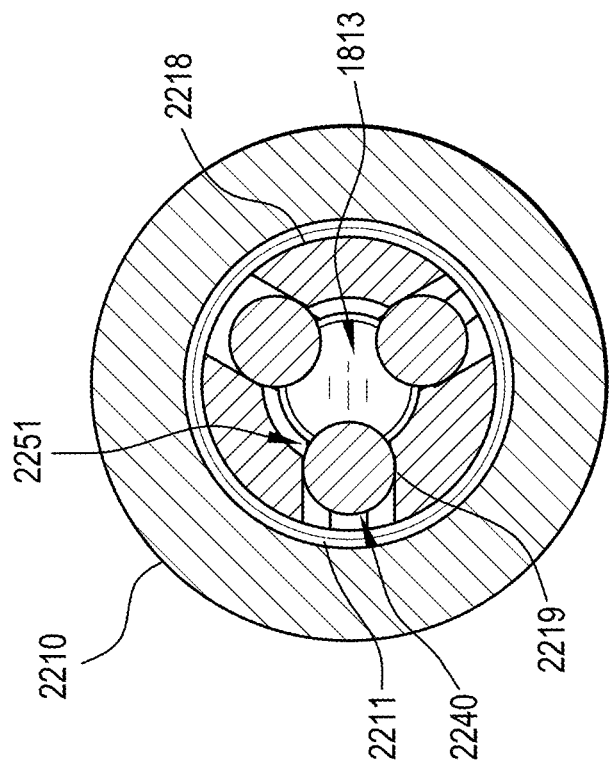
FIG. 13A is a top cross-sectional view of the driver-specific backout prevention assembly of FIGS. 11A-12H with a backout prevention driver tip disposed in the socket of the screw.
Figure 13B:
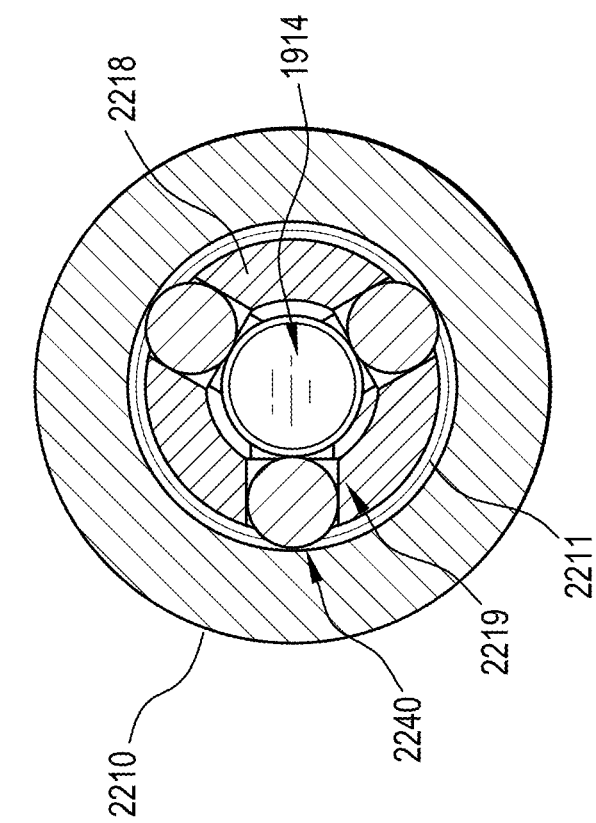
FIG. 13B is a top cross-sectional view of the assembly of FIG. 13A with a standard driver tip disposed in the socket of the screw.

FIGS. 13A and 13B are top cross-sectional views through the lower socket 2250 of the driver-specific backout prevention assembly of FIGS. 11A-12H, with FIG. 13A showing the ball bearings 2240 in their displaced position (e.g., by the safety feature 1914 disposed in the lower socket 2250) and FIG. 13B showing the ball bearings 2240 in a 'free' position when there is sufficient room in the lower socket 2250 for the ball bearings to be moved inwardly beyond being able to interfere with the flange 2211 when the standard driver trip 1813 is disposed in the socket. In some examples, and as illustrated in FIG. 13B, the channel 2219 can include an inner abutment 2251 to prevent the ball bearings from falling into the lower socket 2250 and out of the channel 2219. In some examples, the channel 2219 can include an outer abutment 2251 to prevent the ball bearings from falling out of the head portion 2218 when the head portion 2218 is removed from the body 2210.

While the locking bodies have been shown as ball bearings 2240, other locking bodies are contemplated, such as pins, which can also include a spring for biasing the locking body inward to ensure that the locking body does not get stuck in an interference position and prevent removal of the screw 519.

Figure 14:
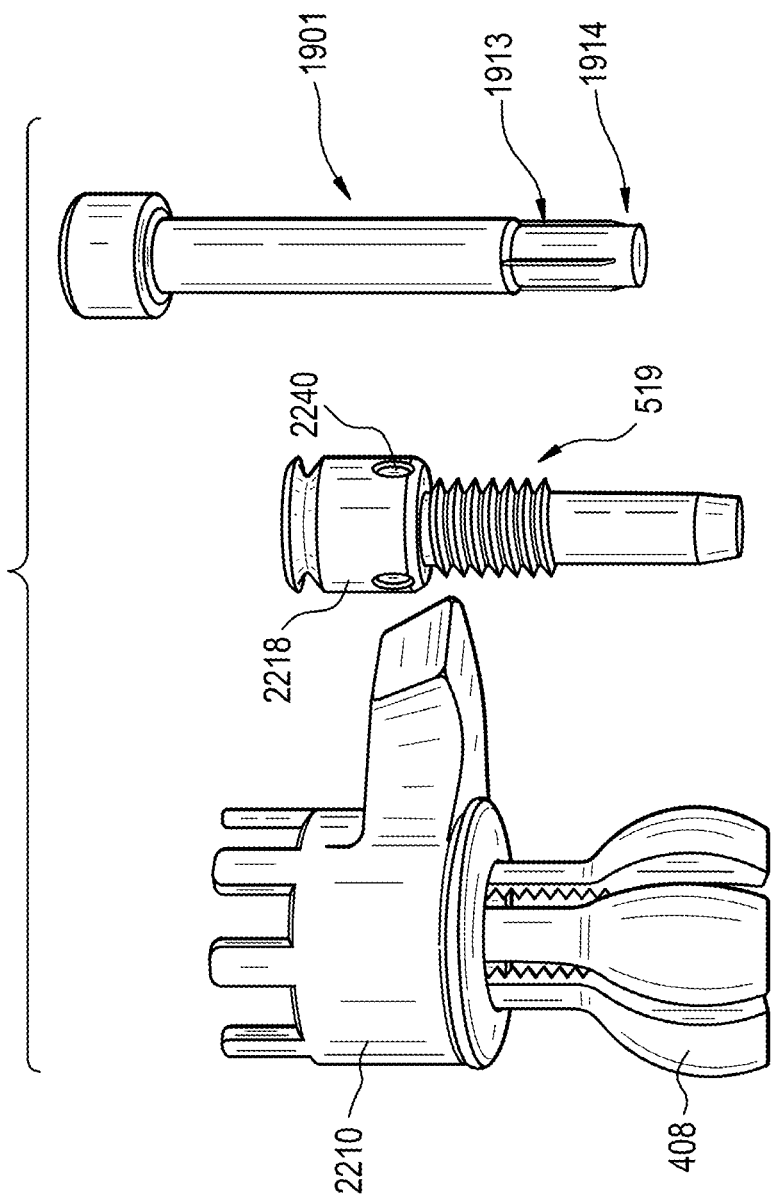
FIG. 14 is a photograph of one embodiment of the driver-specific backout prevention assembly of FIGS. 11A-12H.

FIG. 14 is a photograph of one embodiment of the driver-specific backout prevention assembly 599 of FIGS. 11A-12H, showing the ball-shaped distal end 408 of a body 2210 having a cavity 2215 (not visible) and a screw 519 configured to be disposed in the body 2210 to adjust the position of a tapered member (not shown) disposed at the end of the screw relative to a conic interior surface of the ball-shaped proximal end 408 for expanding the ball-shaped proximal end 408. The head portion 2218 of the screw 519 includes ball bearings 2240 disposed in the channels 2219. FIG. 14 also shows an example backout prevention driver 1901 having a driver 1913 and a interference element 1914 configured to engage with the socket of the head portion 2218, as described herein.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages based on the above-described embodiments. Accordingly, the disclosure is not to be limited by what has been particularly shown and described. All publications and references cited herein are expressly incorporated herein by reference in their entirety

What is claimed is:

1. A backout prevention mechanism comprising:
    a body configured to receive a fastener, the body defining
        a cavity configured to receive a head of the fastener when the fastener is disposed in the body, the cavity having an inwardly extending flange defining a proximal opening of the cavity;
    a fastener having a threaded portion and a head portion, the head portion comprising:
        an upper socket configured to interface with a driver for adjusting a position of the fastener within the body;
        a lower socket; and
        at least one channel radially extending from the lower socket and sized and shaped to allow translation of a locking body through the channel; and
    a locking body disposed in each of the at least one radially extending channels,
    wherein the backout prevention mechanism has a first configuration when the head portion of the fastener is engaged by a first driver and a second configuration when the head portion of the fastener is engaged by a second driver,
    wherein, in the first configuration, engagement of a drive portion of the first driver with the upper socket of the head portion allows the locking body to move radially inward in the channel such that the fastener can be inserted distally into the body and removed proximally from the body without interference between the locking body and the flange of the cavity, and
    wherein, in the second configuration, when the fastener is disposed in the body such that the at least one radially extending channel is disposed distal to the flange of the cavity, engagement of a drive portion of the second driver with the upper socket includes engagement of a distal end portion of the second driver with the lower socket of the head portion that displaces the locking body radially outward such that the locking body interferes with the flange of the channel when the fastener is advanced proximally by the second driver such that the fastener cannot be removed from the body by the second driver.

2. The backout prevention mechanism of claim 1, wherein the locking body is a ball bearing.

3. The backout prevention mechanism of claim 1, wherein the cavity defines a length below the flange, the length of the cavity defining a maximum possible adjustment distance for the fastener in the body in the second configuration.

4. The backout prevention mechanism of claim 1, wherein the cavity defines a cylindrical inner wall, and wherein the flange is a radial flange.

5. The backout prevention mechanism of claim 4, wherein the inner wall of the cavity defines a width that is larger than a diameter of the head portion of the fastener plus twice an extension distance of the locking body from the head portion in the second configuration.

6. The backout prevention mechanism of claim 1, wherein the radially extending channel is configured to retain the locking body in a radially extending direction.

7. The backout prevention mechanism of claim 1, wherein the lower socket defines a cylindrical inner wall.

8. The backout prevention mechanism of claim 1, wherein the upper socket defines a shape configured to interface with a shape of the drive portion of the first and second drivers and enable torque to be delivered from the drive portion of the first and second drivers to the fastener for adjusting a position of the fastener in the body.

9. The backout prevention mechanism of claim 1, wherein the body comprises a threaded portion configured to receive the threaded portion of the fastener.

10. The backout prevention mechanism of claim 1, wherein, in the first configuration, a maximum engagement position of the drive portion of the first driver with the upper socket of the head portion is defined by contact between a drive shaft of the first driver and the upper socket.

11. The backout prevention mechanism of claim 1, wherein, in the second configuration, a maximum engagement position of the distal end portion of the second driver is defined by contact between the distal end portion and a bottom of the lower socket.

12. The backout prevention mechanism of claim 1, wherein, in at least one of the first or second configurations, a maximum engagement position of the drive portion is defined by contact between drive features of the drive portion and an end of corresponding drive features in the upper socket.

13. A surgical instrument, comprising:
    a retractor body configured to couple to an implantable anchor;
    a first tissue manipulating implement coupled to the retractor body and capable of polyaxial movement relative thereto; and
    a second tissue manipulating implement coupled to the retractor body and capable of polyaxial movement relative thereto;
    wherein each of the first and second tissue manipulating implements couples to the retractor body via a polyaxial joint,
    wherein each joint includes a screw to selectively lock the polyaxial joint against movement, and
    wherein each manipulating implement and screw comprises the backout prevention mechanism of claim 1, wherein each manipulating implement comprises the body of the backout prevention mechanism and the screw comprises the fastener of the backout prevention mechanism.

14. The instrument of claim 13, wherein the first and second tissue manipulating implements are opposed to one another such that they can move any of toward and away from one another.

15. The instrument of claim 13, further comprising a lock coupled to the body and configured to interface with an anchor extension to selectively lock a position of the body relative to the anchor extension.

16. The instrument of claim 13, wherein each polyaxial joint comprises a ball and socket joint.

17. The instrument of claim 16, wherein each of the ball and socket joints includes an expanding member configured to selectively lock the ball and socket joint against movement.

18. A backout prevention system comprising:
a body configured to receive a fastener, the body defining a cavity configured to receive a head of the fastener when the fastener is disposed in the body, the cavity defining an inwardly extending flange at a proximal location of the cavity;
a fastener having a threaded portion and a head portion, the head portion comprising:
an upper socket configured to interface with a driver for adjusting a position of the fastener within the body;
a lower socket; and
at least one channel radially extending from the lower socket and sized and shaped to allow translation of a locking body through the channel; and
a locking body disposed in each of the at least one radially extending channels of the fastener; and
a locking driver comprising a distal end region sized and shaped to engage both the upper socket and lower socket, the distal end region having a drive portion and a locking portion located distal to the drive portion, wherein the drive portion is configured to interface with the upper socket for delivering torque to the fastener for adjusting a position of the fastener in the body, and wherein the locking portion is configured to be disposed in the lower socket when the drive portion is interfaced with the upper socket and is sized and shaped to displace the locking body radially outward to a position that prevents the locking body in the fastener from being moved proximally past the flange,
wherein a standard driver comprising a distal end having a drive portion without a locking portion sized and shaped to move the locking body radially outward is able to deliver a torque to the upper socket to adjust the position of fastener in the body proximally and distally without interference between the locking body and the flange.

19. The backout prevention system of claim 18,
wherein the body is a first body, the system further comprising a second body configured to couple to an implantable anchor,
wherein the first body defines at least a portion of a manipulating implement configured to be connected to the second body and capable of polyaxial movement relative thereto,
wherein the tissue manipulating implement couples to the second body via a polyaxial joint, and
wherein the position of the fastener in the first body selectively locks the polyaxial joint against movement.

20. A method of assembling and adjusting a position of a fastener in a locking mechanism, the method comprising:
inserting the fastener into a body of the locking mechanism;
coupling a first driver to the fastener and threading the fastener distally into engagement with the body using the first driver such that a locking body disposed in a radially extending channel of the fastener is disposed distal to an inwardly extending flange in a cavity of the body;
with the fastener in threaded engagement with the body, coupling a second driver to the fastener, the second driver displacing the locking body radially outward such that the locking body interferes with the flange of the channel to prevent proximal movement of the fastener beyond a location where the locking body interfaces with the flange; and
adjusting the position of the fastener in the body using the second driver by threading the fastener between a maximum proximal location defined by the interference between the locking body and the flange and a maximum distal location.

21. The method of claim 20, wherein the locking body is a ball bearing.

22. The method of claim 20, wherein the body comprises a collet disposed in a socket, and wherein the inserting the fastener into the body includes coupling a distal end of the fastener to an expanding member disposed in the collet such that adjusting the position of the fastener in the body expands and contracts the collet in the socket and adjusts a level of frictional engagement between the collet and the socket.

23. The method of claim 22, wherein the body is a first body that defines at least a portion of a manipulating implement and the socket is part of a second body that is configured to couple to an implantable anchor, and the method further includes coupling the collet to the socket after inserting the fastener to the first body with the first driver, the collet and socket defining a polyaxial joint, and wherein adjusting the position of the fastener in the body using the second driver includes selectively locking the polyaxial joint against movement.

* * * * *